US011259768B2

(12) United States Patent
Fukuchi

(10) Patent No.: US 11,259,768 B2
(45) Date of Patent: Mar. 1, 2022

(54) APPARATUS AND METHOD FOR BETA-EMISSION TWO-DIMENSIONAL IMAGING

(71) Applicant: RIKEN, Saitama (JP)

(72) Inventor: Tomonori Fukuchi, Saitama (JP)

(73) Assignee: RIKEN, Saitama (JP)

( * ) Notice: Subject to any disclaimer, the term of this patent is extended or adjusted under 35 U.S.C. 154(b) by 118 days.

(21) Appl. No.: 16/490,276

(22) PCT Filed: Feb. 26, 2018

(86) PCT No.: PCT/JP2018/007009
§ 371 (c)(1),
(2) Date: Aug. 30, 2019

(87) PCT Pub. No.: WO2018/159548
PCT Pub. Date: Sep. 7, 2018

(65) Prior Publication Data
US 2020/0022667 A1    Jan. 23, 2020

(30) Foreign Application Priority Data
Mar. 1, 2017   (JP) .............................. JP2017-038201

(51) Int. Cl.
*A61B 6/00*    (2006.01)
*A61B 5/06*    (2006.01)
(Continued)

(52) U.S. Cl.
CPC .............. *A61B 6/5235* (2013.01); *A61B 5/06* (2013.01); *G01T 1/161* (2013.01); *A61B 6/037* (2013.01)

(58) Field of Classification Search
CPC .. A61B 6/037; A61B 6/12; A61B 6/42; A61B 6/4208; A61B 6/4241;
(Continued)

(56) References Cited

U.S. PATENT DOCUMENTS 4,914,300 A  *  4/1990  Kalish ..................... G01T 1/204
                                                   250/362
6,392,236 B1 *  5/2002  Maekawa ............. G01T 1/2008
                                                   250/369
(Continued)

FOREIGN PATENT DOCUMENTS

JP       2008-209336 A     9/2008
JP          5526435 B2     6/2014
JP       2017-504813 A     2/2017
WO     2009-093396 A1     7/2009

OTHER PUBLICATIONS

International Search Report issued in corresponding International Application No. PCT/JP2018/007009 dated May 29, 2018 (3 pages).

*Primary Examiner* — Anastasia Midkiff
(74) *Attorney, Agent, or Firm* — Osha Bergman Watanabe & Burton LLP

(57) ABSTRACT

An apparatus for beta-emission two-dimensional imaging including: a beta ray detector configured to receive, from an imaging target containing a first nuclide and a second nuclide, a beta ray based on the first or second nuclide and thereby detect the beta ray, the beta ray detector outputting a beta ray detection signal including location information indicating a detection location of the beta ray on a two-dimensional basis; a gamma ray detector configured to detect a gamma ray, the gamma ray detector detecting the first and second peculiar gamma rays in a discriminable manner; and an imaging processor configured to be capable of generating a distribution image of the first nuclide and a distribution image of the second nuclide in a discriminable manner.

5 Claims, 13 Drawing Sheets

(51) Int. Cl.
*G01T 1/161* (2006.01)
*A61B 6/03* (2006.01)

(58) Field of Classification Search
CPC ..... A61B 6/4258; A61B 6/482; A61B 6/5235; A61B 2562/06; G01T 1/16; G01T 1/1603; G01T 1/1606; G01T 1/161; G01T 1/164; G01T 1/1641; G01T 1/1642; G01T 1/1644; G01T 1/20; G01T 1/2006; G01T 1/2018; G01T 1/29; G01T 1/2914; G01T 1/2921; G01T 1/2985; G01N 23/20; G01N 23/20008; G01N 23/20066; G01N 23/22; G01N 23/221; G01N 2033/0093; G01N 2223/01; G01N 2223/05; G01N 2223/056; G01N 2223/0563; G01N 2223/07; G01N 2223/071; G01N 2223/074; G01N 2223/1013; G01N 2223/102; G01N 2223/302; G01N 2223/423; G01N 2223/507
See application file for complete search history.

(56) References Cited

U.S. PATENT DOCUMENTS

| | | | | |
|---|---|---|---|---|
| 7,683,334 | B2* | 3/2010 | Farsoni | G01T 1/2008 250/367 |
| 8,565,860 | B2* | 10/2013 | Kimchy | A61B 5/07 600/436 |
| 8,916,829 | B2* | 12/2014 | Cadieux | G01T 1/204 250/362 |
| 9,018,586 | B2* | 4/2015 | Akers | G01T 1/2008 250/362 |
| 2007/0051892 | A1* | 3/2007 | Warburton | G01T 1/2928 250/362 |
| 2008/0260100 | A1* | 10/2008 | Tarancon Sanz | G01T 1/003 378/66 |
| 2009/0261261 | A1* | 10/2009 | Rodgers | G01T 1/2008 250/370.11 |
| 2013/0299709 | A1* | 11/2013 | Forster | G01T 3/00 250/366 |
| 2014/0175293 | A1 | 6/2014 | Fukuchi et al. | |

* cited by examiner

EXAMPLE OF TYPE A

EXAMPLE OF TYPE B

TYPE B EVENT (PECULIAR GAMMA RAY DETECTION SUCCESSFUL)

TYPE B EVENT (PECULIAR GAMMA RAY DETECTION FAILED)

NEGATIVE BETA DECAY EVENT

REFERENCE IMAGING APPARATUS

APPARATUS AND METHOD FOR BETA-EMISSION TWO-DIMENSIONAL IMAGING

TECHNICAL FIELD

The present invention relates to an apparatus and a method for beta-emission two-dimensional imaging.

LIST OF CITATIONS

Patent Literature

Patent Document 1: Japanese Patent registered as No. 5526435

BACKGROUND ART

As one type of diagnostic equipment, positron emission tomography (PET) systems are in practical use. A PET system employs the type of positive beta decay ($\beta^+$ decay) that emits positrons (also called positron emission decay): it detects the two gamma rays that are emitted when an emitted positron annihilates with a neutron in a material, and thereby estimates the distribution of the radioactive nuclide that undergoes such beta decay. For example, a drug that concentrates in cancerous cells can be labeled with a positron emitting nuclide; then a living body administered with the drug can be, as an imaging target, imaged on a PET system to acquire a three-dimensional distribution image of cancerous cells in the living body.

As life science and medicine progress, more and more light is shed on how a vital function or a focus of disease manifests itself through complicated intertwining of different kinds of molecular behavior. In keeping with that, research is being carried out on methods (hereinafter referred to as multiple molecular simultaneous imaging) involving administering a living body with a plurality of drugs labeled with different radioactive nuclides so that the distribution of nuclides in the living body is imaged at once in a manner that permits discrimination among the different nuclides. A configuration for performing multiple molecular simultaneous imaging on a PET system is seen in Patent Document 1.

On the other hand, in radiography using radiation such as X-rays, there is used, as a substitute for photographic film, what is called a flat-panel detector, that is, an imaging apparatus that has an array of semiconductor-based imaging elements disposed on a flat face. The flat-panel detector can directly read radiation-induced ionization inside a material, and is becoming increasingly widespread in the medical scene.

In addition to the flat-panel detector just mentioned, also widespread in the field of basic research is an imaging plate, which allows read-out, with laser light or the like, of the two-dimensional distribution of chemical changes brought about, according to the amount of, radiation exposed to. With the imaging plate, two-dimensional information on an imaging target can be acquired with a simple configuration. Compared with the film, the imaging plate is more sensitive, and is reusable, after read-out, with the acquired information erased through, for example, exposure to white light. Thus, the imaging plate is used to survey the distribution of beta-ray emitting nuclides in tissue sections and cultured cells. Inconveniently, however, all these apparatus are configured to measure the integrated amount of energy of all radiation incident on a given spot during the imaging duration; they do not give the energy and the time of incidence of different types of incident radiation individually.

Meanwhile, recent years have seen the emergence of a technology, directed to radiation imaging detectors, that can calculate energy and time of incidence through event-by-event signal processing (the technology being called "photon counting" when it reads out photons in particular). This technology is applied to CT systems and the like where, for X-rays of different energies, their energies are, at every event, discriminated and converted into an image to identify a material based on the fact that a material absorbs X-rays of different energies at different absorptances.

In photon counting-type measurement, unlike in integral measurement of the total energy within the imaging duration, it is necessary to perform, on an event-by-event basis, signal processing on information at each imaging element. This requires as many on-line one-event signal processing circuits as the number of imaging elements. Imaging elements with a high resolution have an accordingly large number of channels. Thus, developing a signal processor with a high degree of integration combined with a high throughput is a challenge toward higher resolutions in photon counting imaging. In fact, in recent years, integrated circuits are becoming increasingly dense, and the number of channels that can be handled is increasing. Thus, even higher resolutions are expected in imaging relying on photon counting.

According to another technique for improved resolution, an enlarged image is acquired by use of, for example, a lens that exploits refraction or reflection of scintillation light (visible light).

SUMMARY OF THE INVENTION

Technical Problem

When an object contains a radioactive nuclide that emits beta rays, by imaging the object as an imaging target with an imaging plate, it is possible to acquire a two-dimensional distribution of the radioactive nuclide inside the object. With a conventional imaging plate, however, if a plurality of nuclides are distributed inside the imaging target, it is impossible to distinguish a particular nuclide from the other nuclides, that is, it is impossible to perform imaging in a manner that permits discrimination among different nuclides. Even such an imaging plate is, if multiple molecular simultaneous imaging can be applied to it, useful because it then permits even finer analysis than is currently the case. The energies of the beta rays emitted by beta decay do not take particular values with particular nuclides but are continuous. Thus, even by use of a photon counting-type detector, it is difficult to distinguish different nuclides.

While the above discussion focuses on circumstances around imaging of a plurality of nuclides, imaging of a single nuclide is needed and useful in various cases. Here, improved resolution in imaging of a single nuclide is useful.

It is therefore one object of the present invention to provide an apparatus and a method for beta-emission two-dimensional imaging that achieve imaging in a manner that permits discrimination among different nuclides. It is another object of the present invention to provide an apparatus and a method for beta-emission two-dimensional imaging that contribute to improved resolution in the imaging of a nuclide.

Means for Solving the Problem

In a daughter nucleus after beta decay, if the atomic nucleus is in an excited state, it transits to the ground state by emitting energy mainly in the form of a gamma ray (a high-energy electromagnetic wave). This gamma ray is generally called a deexcitation gamma ray, and has an energy peculiar to a given nuclide. Accordingly, in the present description, it is called a "peculiar gamma ray" for distinction from a gamma ray that results from annihilation between a positron and an electron.

According to one aspect of the present invention, an apparatus for beta-emission two-dimensional imaging includes:

a beta ray detector configured to receive, from an imaging target containing a first nuclide and a second nuclide, a beta ray based on the first or second nuclide and thereby detect the beta ray, the beta ray detector outputting a beta ray detection signal including location information indicating the detection location of the beta ray on a two-dimensional basis, the first nuclide transiting to an excited state of the daughter nucleus by beta decay and, subsequently to emission of a beta ray by beta decay, transiting to the ground state of the daughter nucleus while emitting a first peculiar gamma ray, the second nuclide transiting to an excited state of the daughter nucleus by beta decay and, subsequently to emission of a beta ray by beta decay, transiting to the ground state of the daughter nucleus while emitting a second peculiar gamma ray having a different energy from the energy of the first peculiar gamma ray;

a gamma ray detector configured to detect a gamma ray, the gamma ray detector detecting the first and second peculiar gamma rays in a discriminable manner; and an imaging processor configured to be capable of generating a distribution image of the first nuclide and a distribution image of the second nuclide in a discriminable manner based on the time point of beta ray detection by the beta ray detector and the time point of gamma ray detection by the gamma ray detector, the location information included in the beta ray detection signal, and which of the first and second peculiar gamma rays is detected in the gamma ray detector.

This makes it possible to image the distribution of a plurality of nuclides at once in a manner that permits discrimination between the nuclides. While a PET system exploiting annihilation can only use a nuclide that undergoes positive beta decay (beta decay accompanied by emission of a positron), the above beta-emission two-dimensional imaging apparatus, owing to employing a method that directly images a beta ray, can use not only a nuclide that undergoes positive beta decay but also a nuclide that undergoes negative beta decay (beta decay accompanied by emission of an electron). This is useful.

According to another aspect of the present invention, an apparatus for beta-emission two-dimensional imaging includes:

a beta ray detector configured to receive, from an imaging target containing a first nuclide and a second nuclide, a beta ray based on the first or second nuclide and thereby detect the beta ray, the beta ray detector outputting a beta ray detection signal including location information indicating the detection location of the beta ray on a two-dimensional basis, the first nuclide transiting to an excited state of the daughter nucleus by beta decay and, subsequently to emission of a beta ray by beta decay, transiting to the ground state of the daughter nucleus while emitting a peculiar gamma ray having a predetermined energy, the second nuclide transiting to a ground state of the daughter nucleus by emitting a beta ray by beta decay;

a gamma ray detector configured to detect a gamma ray which may be the peculiar gamma ray; and an imaging processor configured to be capable of generating a distribution image of the first nuclide and another distribution image reflecting the distribution of the second nuclide in a discriminable manner based on the time point of beta ray detection by the beta ray detector and the time point of gamma ray detection by the gamma ray detector, the location information included in the beta ray detection signal, and whether the peculiar gamma ray is detected in the gamma ray detector.

This makes it possible to image the distribution of a plurality of nuclides at once in a manner that permits discrimination between the nuclides (in a manner that permits discrimination of at least the first nuclide from any other nuclide). While a PET system exploiting annihilation can only use a nuclide that undergoes positive beta decay (beta decay accompanied by emission of a positron), the above beta-emission two-dimensional imaging apparatus, owing to employing a method that directly images a beta ray, can use not only a nuclide that undergoes positive beta decay but also a nuclide that undergoes negative beta decay (beta decay accompanied by emission of an electron). This is useful.

According to yet another aspect of the present invention, an apparatus for beta-emission two-dimensional imaging includes:

a beta ray detector configured to receive, from an imaging target containing a first nuclide and a second nuclide, a beta ray based on the first or second nuclide and thereby detect the beta ray, the beta ray detector outputting a beta ray detection signal including location information indicating the detection location of the beta ray on a two-dimensional basis, the first nuclide emitting a positron as a beta ray by positive beta decay, the second nuclide emitting an electron as a beta ray by negative beta decay;

a gamma ray detector configured to detect a gamma ray which may be an annihilation gamma ray resulting from annihilation of the positron as the beta ray from the first nuclide with an electron in the beta ray detector; and an imaging processor configured to be capable of generating a distribution image of the first nuclide and another distribution image reflecting the distribution of the second nuclide in a discriminable manner based on the time point of beta ray detection by the beta ray detector and the time point of gamma ray detection by the gamma ray detector, the location information included in the beta ray detection signal, and whether the annihilation gamma ray is detected in the gamma ray detector.

This makes it possible to image the distribution of a plurality of nuclides at once in a manner that permits discrimination between the nuclides (in a manner that permits discrimination of at least the first nuclide from any other nuclide). While a PET system exploiting annihilation can only use a nuclide that undergoes positive beta decay (beta decay accompanied by emission of a positron), the above beta-emission two-dimensional imaging apparatus, owing to employing a method that directly images a beta ray, can use not only a nuclide that undergoes positive beta decay but also a nuclide that undergoes negative beta decay (beta decay accompanied by emission of an electron). This is useful.

According to still another aspect of the present invention, an apparatus for beta-emission two-dimensional imaging includes:

a beta ray detector configured to receive, from an imaging target containing a nuclide, a beta ray based on the nuclide and thereby detect the beta ray, the beta ray detector outputting a beta ray detection signal including location information indicating the detection location of the beta ray on a two-dimensional basis, the nuclide transiting to an excited state of the daughter nucleus by beta decay and, subsequently to emission of a beta ray by beta decay, transiting to the ground state of the daughter nucleus while emitting a peculiar gamma ray, a gamma ray detector configured to detect a gamma ray which may be the peculiar gamma ray; and an imaging processor configured to be capable of generating a distribution image of the nuclide based on the time point of beta ray detection by the beta ray detector and the time point of gamma ray detection by the gamma ray detector, the location information included in the beta ray detection signal, and whether the peculiar gamma ray is detected in the gamma ray detector.

With the beta-emission two-dimensional imaging apparatus configured as described above, it is possible to generate a distribution image of the nuclide based on the location information obtained when the peculiar gamma ray is detected in the gamma ray detector. When the peculiar gamma ray is detected in the gamma ray detector, the peculiar gamma ray is not incident on the beta ray detector. Thus, the location information obtained when the peculiar gamma ray is detected in the gamma ray detector is limited to information on the detection location of a beta ray. By generating a distribution image of the nuclide based on that detection location information, it is possible to generate a distribution image with high resolution. Why the so generated distribution image has high resolution will be clarified further on in the description.

According to a further aspect of the present invention, a method for beta-emission two-dimensional imaging includes:

a beta ray detecting step of receiving, from an imaging target containing a first nuclide and a second nuclide, a beta ray based on the first or second nuclide, thereby detecting the beta ray, and then obtaining a beta ray detection signal including location information indicating the detection location of the beta ray on a two-dimensional basis, the first nuclide transiting to an excited state of the daughter nucleus by beta decay and, subsequently to emission of a beta ray by beta decay, transiting to the ground state of the daughter nucleus while emitting a first peculiar gamma ray, the second nuclide transiting to an excited state of the daughter nucleus by beta decay and, subsequently to emission of a beta ray by beta decay, transiting to the ground state of the daughter nucleus while emitting a second peculiar gamma ray having a different energy from the energy of the first peculiar gamma ray;

a gamma ray detecting step of detecting a gamma ray, the gamma ray detecting step involving detecting the first and second peculiar gamma rays in a discriminable manner; and an imaging processing step capable of generating a distribution image of the first nuclide and a distribution image of the second nuclide in a discriminable manner based on the time point of beta ray detection in the beta ray detecting step and the time point of gamma ray detection in the gamma ray detecting step, the location information included in the beta ray detection signal, and which of the first and second peculiar gamma rays is detected in the gamma ray detecting step.

According to a further aspect of the present invention, a method for beta-emission two-dimensional imaging includes:

a beta ray detecting step of receiving, from an imaging target containing a first nuclide and a second nuclide, a beta ray based on the first or second nuclide, thereby detecting the beta ray, and then obtaining a beta ray detection signal including location information indicating the detection location of the beta ray on a two-dimensional basis, the first nuclide transiting to an excited state of the daughter nucleus by beta decay and, subsequently to emission of a beta ray by beta decay, transiting to the ground state of the daughter nucleus while emitting a peculiar gamma ray having a predetermined energy, the second nuclide transiting to the ground state of the daughter nucleus by emitting a beta ray by beta decay;

a gamma ray detecting step of detecting a gamma ray which may be the peculiar gamma ray; and an imaging processing step capable of generating a distribution image of the first nuclide and another distribution image reflecting the distribution of the second nuclide in a discriminable manner based on the time point of beta ray detection in the beta ray detecting step and the time point of gamma ray detection in the gamma ray detecting step, the location information included in the beta ray detection signal, and whether the peculiar gamma ray is detected in the gamma ray detecting step.

According to a further aspect of the present invention, a method for beta-emission two-dimensional imaging includes:

a beta ray detecting step of receiving, from an imaging target containing a first nuclide and a second nuclide, a beta ray based on the first or second nuclide, thereby detecting the beta ray, and then obtaining a beta ray detection signal including location information indicating the detection location of the beta ray on a two-dimensional basis, the first nuclide emitting a positron as a beta ray by positive beta decay, the second nuclide emitting an electron as a beta ray by negative beta decay;

a gamma ray detecting step of detecting a gamma ray which may be an annihilation gamma ray resulting from annihilation of the positron as the beta ray from the first nuclide with an electron in the beta ray detector; and an imaging processing step capable of generating a distribution image of the first nuclide and another distribution image reflecting the distribution of the second nuclide in a discriminable manner based on the time point of beta ray detection in the beta ray detecting step and the time point of gamma ray detection in the gamma ray detecting step, the location information included in the beta ray detection signal, and whether the annihilation gamma ray is detected in the gamma ray detecting step.

According to a further aspect of the present invention, a method for beta-emission two-dimensional imaging includes:

a beta ray detecting step of receiving, from an imaging target containing a nuclide, a beta ray based on the nuclide, thereby detecting the beta ray, and then obtaining a beta ray detection signal including location information indicating the detection location of the beta ray on a two-dimensional basis, the nuclide transiting to an excited state of the daughter nucleus by beta decay and, subsequently to emission of a beta ray by beta decay, transiting to the ground state of the daughter nucleus while emitting a peculiar gamma ray, a gamma ray detecting step of detecting a gamma ray which may be the peculiar gamma ray; and an imaging processing step capable of generating a distribution image of the nuclide based on the time point of beta ray detection in the beta ray detecting step and the time point of gamma ray detection in the gamma ray detecting step, the location information included in the beta ray detection signal, and whether the peculiar gamma ray is detected in the gamma ray detecting step.

Advantageous Effects of the Invention

According to the present invention, it is possible to provide an apparatus and a method for beta-emission two-dimensional imaging that achieve imaging in a manner that permits discrimination between different nuclides. According to the present invention, it is possible to provide an apparatus and a method for beta-emission two-dimensional imaging that contribute to improved resolution in the imaging of a nuclide.

DESCRIPTION OF EMBODIMENTS

Hereinafter, examples embodying the present invention will be described specifically with reference to the accompanying drawings. Among the diagrams referred to, the same parts are identified by the same reference signs, and in principle no overlapping description of the same parts will be repeated. In the present description, for the sake of simple description, symbols and other designations referring to information, signals, physical quantities, components, and the like are occasionally used with the names of the corresponding information, signals, physical quantities, components, and the like omitted or abbreviated.

Figure 1:
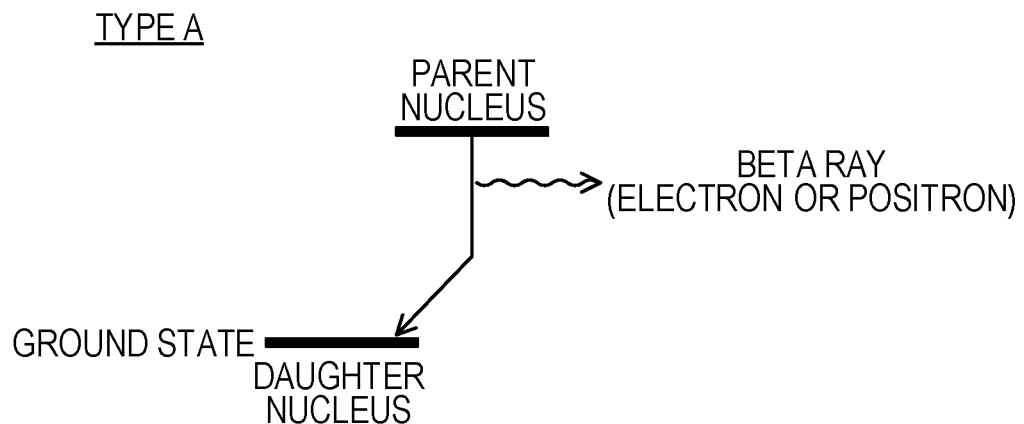
FIG. 1 is a diagram showing the mode of type A radioactive decay assumed in an embodiment of the present invention.
Figure 2:
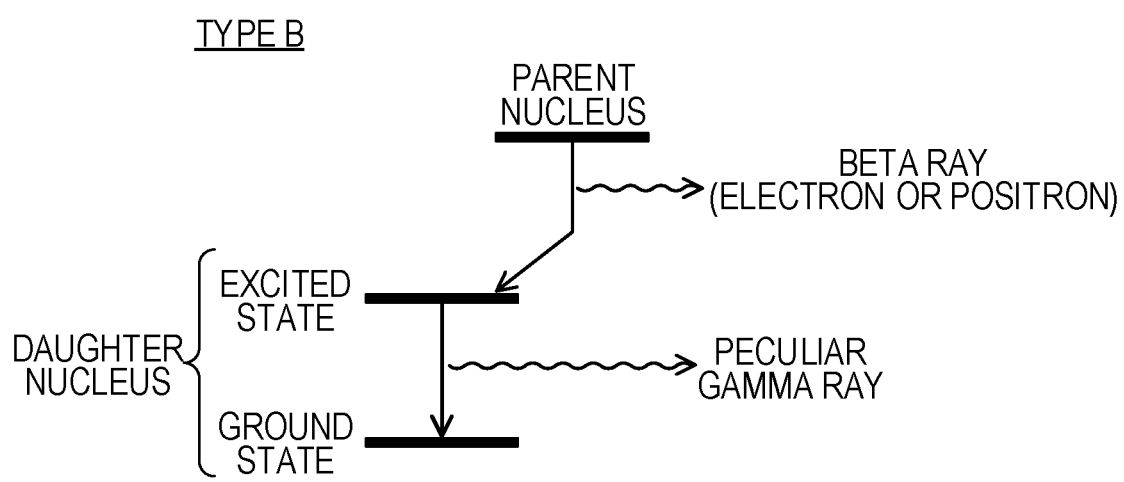
FIG. 2 is a diagram showing the mode of type B radioactive decay assumed in an embodiment of the present invention.

First, with reference to FIGS. 1 and 2, a description will be given of two modes of radioactive decay of a radioactive nuclide (a nuclide with radioactivity). FIG. 1 shows a type A mode of radioactive decay, and FIG. 2 shows a type B mode of radioactive decay. Radioactive nuclides that undergo radioactive decay in the type A and type B modes are referred to as type A and type B nuclides respectively. With respect to a given radioactive nuclide, the nuclide before beta decay is referred to as the parent nucleus, and the nuclide after beta decay is referred to as the daughter nucleus.

As shown in FIG. 1, in a type A nuclide, the parent nucleus undergoes beta decay to transit to the daughter nucleus in the ground state. That is, through beta decay, the energy level of a type A nuclide transits from the energy level of the parent nucleus to the energy level of the daughter nucleus in the ground state. In a type A nuclide, beta decay can be negative beta decay accompanied by emission of an electron (a beta particle with a negative charge) or positive beta decay accompanied by emission of a positron (a beta particle with a positive charge). That is, through beta decay, a type A nuclide emits a beta ray of an electron or a positron. In type A beta decay, as opposed to type B beta decay, which will be described later, no gamma ray is emitted (even if a gamma ray is emitted, it is disregarded on the imaging apparatus 1, described later, according to an embodiment.

As shown in FIG. 2, in a type B nuclide, the parent nucleus undergoes beta decay to transit to the daughter nucleus in an excited state, and subsequently this, that is, the daughter nucleus in the excited state, undergoes gamma decay by emitting a gamma ray with an energy peculiar to the type B nuclide (hereinafter referred to as a peculiar gamma ray) to transit to the daughter nucleus in the ground state. The energy difference of the daughter nucleus of the type B nuclide between the excited and ground states is the energy of the peculiar gamma ray. In a type B nuclide, the time point at which the peculiar gamma ray is emitted is dictated by a quantum-mechanical probability that depends on the structure of the nucleus. An index of the life-span from the excited state to the ground state of the daughter nucleus is given as a half-life. Also in a type B nuclide, as in a type A nuclide, beta decay can be negative beta decay accompanied by emission of an electron (a beta particle with a negative charge) or positive beta decay accompanied by emission of a positron (a beta particle with a positive charge). That is, through beta decay, a type B nuclide emits a beta ray of an electron or a positron.

Figure 3:
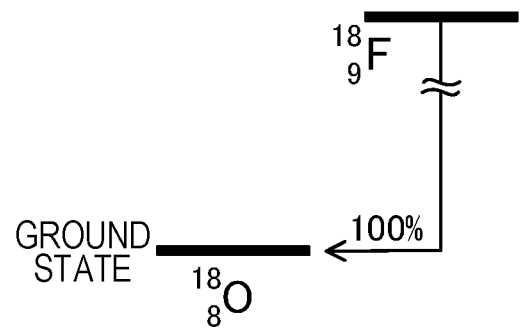
FIG. 3 is a diagram showing a specific example of type A radioactive decay assumed in an embodiment of the present invention.

FIG. 3 shows one example of type A radioactive decay. When $^{18}$F, which is the parent nucleus of a type A nuclide, undergoes beta decay, it transits to the ground state of $^{18}$O, which is the daughter nucleus, with a probability of 100%. The beta decay here is positive beta decay, and thus through this beta decay, a positron is emitted.

Figure 4:
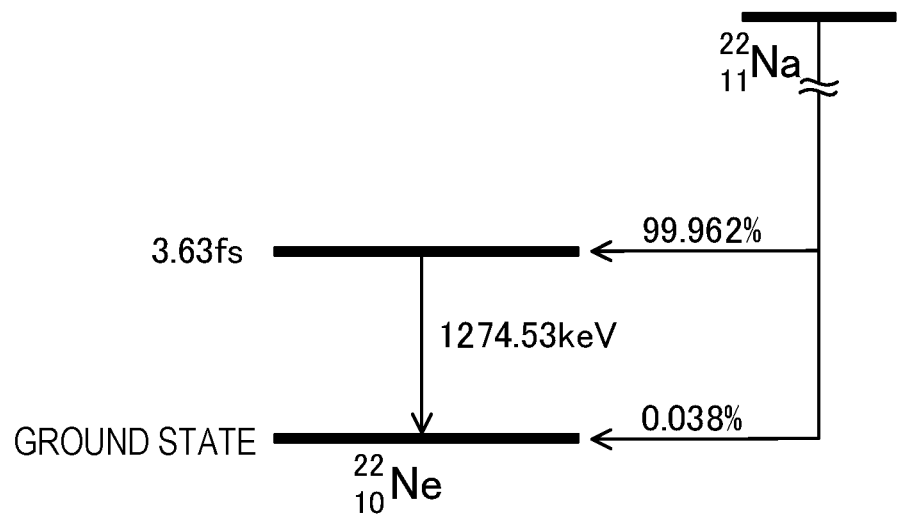
FIG. 4 is a diagram showing a specific example of type B radioactive decay assumed in an embodiment of the present invention.

FIG. 4 shows one example of type B radioactive decay. $^{22}$Na, which is the parent nucleus of a type B nuclide, goes through an excited state of $^{22}$Ne, which is the daughter nucleus, with a probability of about 99.96% before transiting to the ground state of $^{22}$Ne. Meanwhile, through gamma decay, the excited state of $^{22}$Ne transits to the ground state of $^{22}$Ne with a half-life of about 3.63 fs (femtoseconds). During this transition, a peculiar gamma ray with an energy of 1275 keV (kiloelectronvolts) is emitted. The beta decay that brings about the transition from $^{22}$Na to the excited state of $^{22}$Ne is positive beta decay, and through this beta decay, a positron is emitted. A type B nuclide can, in the process of transiting from the parent nucleus to the ground state of the daughter nucleus, go through a plurality of excited states of the daughter nucleus.

[Outline of the Configuration of an Imaging Apparatus]

Figure 5:
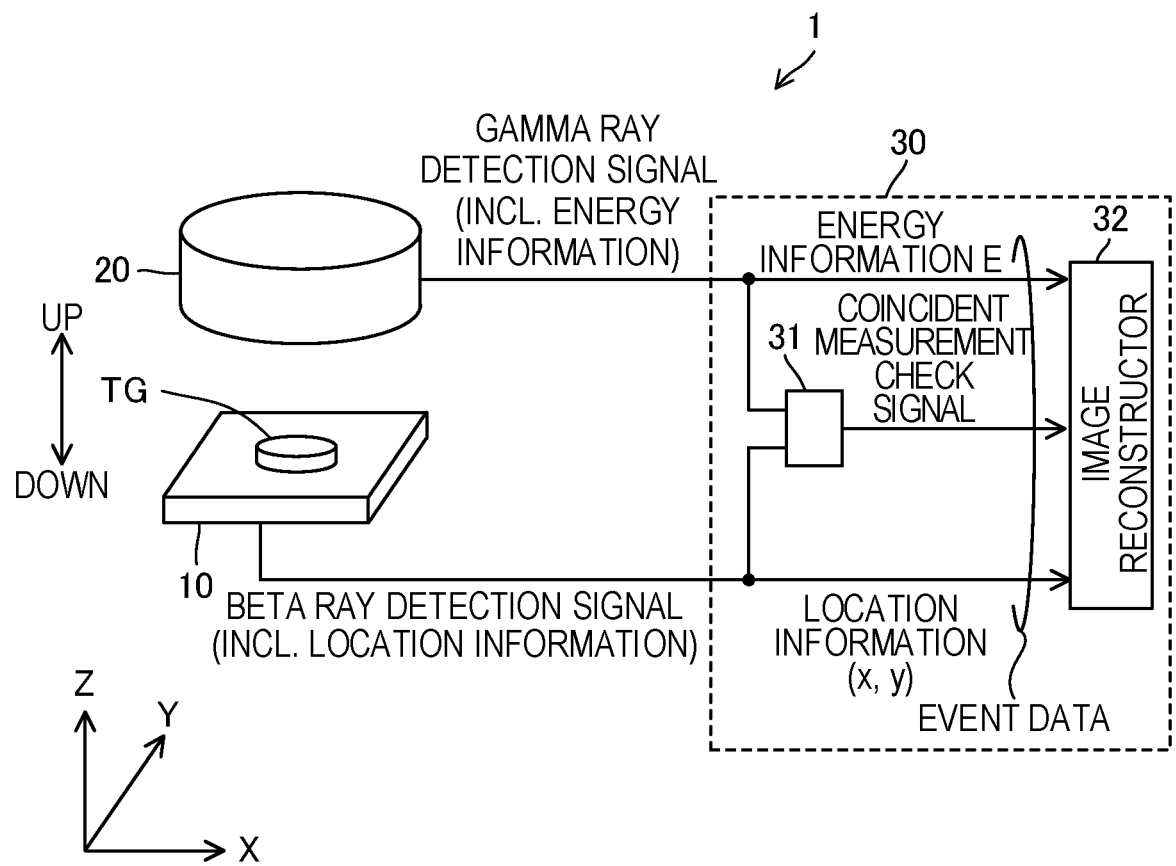
FIG. 5 is a diagram showing an outline of the configuration of an imaging apparatus according to an embodiment of the present invention.

FIG. 5 is a diagram showing an outline of the configuration of an imaging apparatus (beta-emission two-dimensional imaging apparatus) 1 according to an embodiment. The imaging apparatus 1 includes: a beta ray detector 10, which is a beta ray detector of a location resolution type; a gamma ray detector 20, which is a gamma ray detector of an energy resolution type; and an imaging processor 30. TG represents an imaging target on the imaging apparatus 1.

It is assumed that, in real space, X-, Y-, and Z-axes are perpendicular to each other, and the three-dimensional space defined by X-, Y-, and Z-axes is referred to as XYZ space. The two-dimensional plane parallel to X- and Y-axes is referred to as XY-plane. The X-, Y-, and Z-axis components of a given location are represented by x, y, and z respectively. The location of a given point in XYZ space is represented by (x, y, z), and its location on XY-plane, with attention paid only to the X- and Y-axis components, is represented by (x, y). For convenience of description, the directions pointing to the positive and negative sides along Z-axis are taken as the upward and downward directions respectively.

The imaging target TG is an object with a two-dimensional shape extending in the X- and Y-axis directions, or an object that can be regarded as an imaging target with a two-dimensional shape. The imaging target TG contains two or more type B nuclides, or contains one or more type A nuclides along with one or more type B nuclides. These nuclides are distributed in the X- and Y-axis directions in the imaging target TG.

A type A or type B nuclide can label a drug. The imaging target TG can contain any type A or type B nuclide in the form incorporated in a drug. A drug labeled with a type A nuclide (that is, a drug that has a type A nuclide incorporated in it) is referred to as a type A probe, and a drug labeled with a type B nuclide (that is, a drug that has a type B nuclide incorporated in it) is referred to as a type B probe.

———Beta Ray Detector———

So that the beta ray detector 10 can receive beta rays emitted from radioactive nuclides in the imaging target TG, the beta ray detector 10 is disposed under the imaging target TG, adjacent to it. The beta ray detector 10 receives and thereby detects beta rays emitted from the radioactive nuclides in the imaging target TG. Every time the beta ray detector 10 detects a beta ray incident on it, it outputs a beta ray detection signal. The beta ray detection signal indicates incidence of a beta ray on the beta ray detector 10, and in addition includes location information on the location on the beta ray detector 10 at which it detected the beta ray. Here, the detection location of the beta ray is a location on XY-plane. That is, the location information in the beta ray detection signal only includes the X- and Y-axis components of the detection location of the beta ray.

Figure 6:
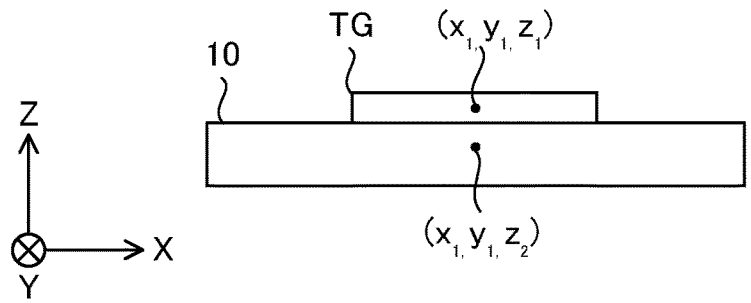
FIG. 6 is a diagram showing a relationship between the presence location of a radioactive nuclide emitting a beta ray and the detection location of the beta ray on the imaging apparatus of FIG. 5.

Since the imaging target TG is an imaging target with a two-dimensional shape while the beta ray has low penetrating power, when a beta ray is detected at location $(x_1, y_1, z_2)$ in the beta ray detector 10, it is the likeliest that the radioactive nuclide that emitted the beta ray is present at location $(x_1, y_1, z_1)$ in the imaging target TG (see FIG. 6). Accordingly, with attention paid only to two-dimensional components, that is, X- and Y-axis components, the detection location of the beta ray can be regarded as the location of the radioactive nuclide that emits the beta ray. That is, the location information included in the beta ray detection signal can be considered to represent the X- and Y-axis components of the location of a beta ray emitting radioactive nuclide in the imaging target TG. Accordingly, it can be said that the beta ray detector 10 detects the location of a beta ray emitting radioactive nuclide in the imaging target TG in two dimensions. Beta ray detectors with this function are well-known, and thus a well-known beta ray detector of a location resolution type can be adopted as the beta ray detector 10.

The beta ray detector 10 may also detect gamma rays. However, since the gamma ray has high penetrating power, when use is made of a beta ray detector 10 with a thickness necessary and sufficient (minimum required thickness, typically several millimeters or less) to block beta rays from the nuclides used in imaging, most gamma rays penetrate the beta ray detector 10.

Figure 7:
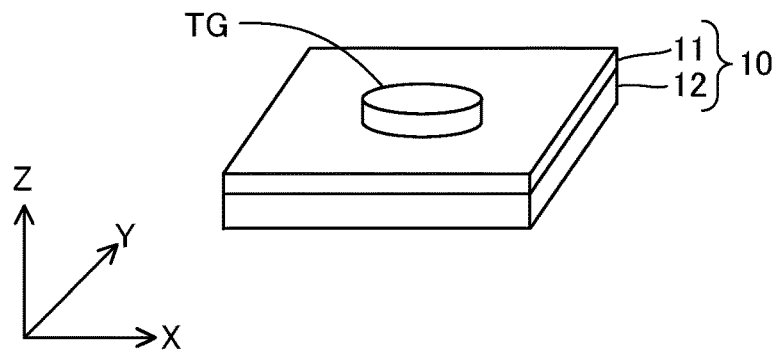
FIG. 7 is a diagram showing an example of the configuration of a beta ray detector in the imaging apparatus of FIG. 5.

Here, it is assumed that, as shown in FIG. 7, the beta ray detector 10 is configured as a scintillation detector that includes a scintillator 11 and a light detector amplifier 12. Any well-known scintillation detector can be used as the beta ray detector 10. The configuration and the function of the scintillator 11 and the light detector amplifier 12 will now be described briefly.

So that the scintillator 11 can receive beta rays emitted from radioactive nuclides in the imaging target TG, the scintillator 11 is disposed under the imaging target TG, adjacent to it. The scintillator 11 is a plate of a scintillator material that extends in the X and Y-axis directions, and emits scintillation light when a beta ray is incident on it. So long as this function is fulfilled, the scintillator 11 may be formed of any scintillator material.

So that the light detector amplifier 12 can receive scintillation light from the scintillator 11, the light detector amplifier 12 is disposed under the scintillator 11, adjacent to it, and is optically coupled to it. Thus, the scintillator 11 is inserted between the imaging target TG and the light detector amplifier 12. The light detector amplifier 12 amplifies the scintillation light from the scintillator 11 and then converts it into an electrical signal, which the light detector amplifier 12 then outputs. More specifically, when scintillation light is incident on it, the light detector amplifier 12 outputs, as a beta ray detection signal, an electrical signal that includes, as the above-mentioned location information (x, y), information indicating the X- and Y-axis components of the location of incidence (detection location) of the scintillation light. With attention paid only to the X- and Y-axis components of the location, the location of incidence of the scintillation light on the light detector amplifier 12 is regarded as the detection location of a beta ray on the beta ray detector 10 (in other words, the location of source of the scintillation light in the scintillator 11), and is regarded as the location of a beta ray emitting radioactive nuclide in the imaging target TG. Here, it is assumed that, as the light detector amplifier 12, use is made of an MPPC (a registered trademark) having an array of avalanche photodiodes (hereinafter referred to as APDs) with a high multiplication factor that operate in a Geiger mode. A Geiger mode refers to a state where APDs are applied with a reverse voltage higher than their breakdown voltage.

Figure 8A:
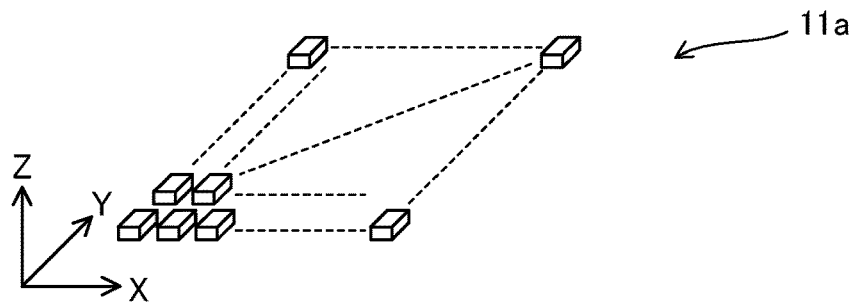
FIG. 8A is a diagram showing an example of the configuration of a scintillator according to an embodiment of the present invention.
Figure 8B:
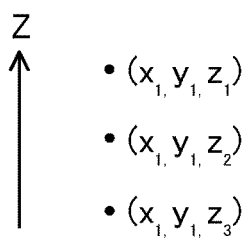
FIG. 8B is a diagram showing a relationship between three locations related to detection of a beta ray.

For enhanced resolution in location detection on the beta ray detector 10, as shown in FIG. 8A, a scintillator 11a formed by dividing a plate of a scintillator material along both the X- and Y-axis directions (that is, a group of so-divided pieces of a scintillator in an array) may be used as the scintillator 11. Of the end faces of each of the divided pieces of the scintillator material, those perpendicular to XY-plane may be laid with a reflective member, or those end faces may be frosted (with irregular asperities formed on the surface). The aim is to reflect or diffuse the scintillation light that reaches those end faces. In a case where the scintillator 11a shown in FIG. 8A is used, a large part of the beta rays emitted from a given location $(x_1, y_1, z_1)$ in the imaging target TG toward the scintillator 11a are incident on the scintillator material at location $(x_1, y_1, z_2)$ right below the given location. The scintillation light generated in the scintillator material is, except for the part of it traveling straight downward, reflected, diffused, or otherwise deflected at the above-mentioned end faces (perpendicular to XY-plane) of the scintillator material. As a result, with a high probability, the scintillation light from the scintillator material reaches location $(x_1, y_1, z_3)$ right below location $(x_1, y_1, z_2)$, and is converted into an electrical signal at location $(x_1, y_1, z_3)$ (see FIG. 8B). It is thus possible to accurately detect the location $(x_1, y_1)$ on XY-plane of a radioactive nuclide that emits a beta ray.

Instead, a single-piece plate of a scintillator material may be used as the scintillator 11 with slits formed in the scintillator material along both the X- and Y-axis directions. This configuration works in a similar manner to the one using the scintillator 11a. In that case, of the end faces of the slits, those perpendicular to XY-plane may be laid with a reflective member so that the scintillation light that reaches those end faces is reflected or diffused, or those end faces may be frosted (with irregular asperities formed on the surface).

Even a single-piece plate of a scintillator material with no slits like those mentioned above formed in it may be used as the scintillator 11. In that case, when scintillation light is generated at location $(x_1, y_1, z_2)$ inside the scintillator 11, the detection location of the scintillation light in the light detector amplifier 12 has a given spread on XY-plane. Even so, with a high probability, the detected intensity of the scintillation light is highest at location $(x_1, y_1)$, and thus, through signal processing, it is possible to roughly image the location $(x_1, y_1)$ that is supposed to be discovered.

In the above description, the light detector amplifier 12 is built by use of an MPPC (a registered trademark); instead, the light detector amplifier 12 may be built by use of APDs that operate in a normal mode, which is different from the Geiger mode. Instead, the light detector amplifier 12 may be built by use of a photomultiplier tube. Instead, the beta ray detector 10 may be built by use of a semiconductor detector that directly detects beta rays without the use of a scintillator 11.

Recent developments in signal processing technology have made available a system that can count radiation ray by ray and determine energy and detection time point as by photon counting even with a semiconductor imaging detector having fine pixels and a large number of channels. Applying such a system to the present invention is expected to make it possible in the future to acquire images with sufficiently high resolutions.

———Gamma Ray Detector———

So that the gamma ray detector 20 can receive gamma rays emitted from radioactive nuclides in the imaging target TG, the gamma ray detector 20 is disposed over the imaging target TG, apart from it. The gamma ray detector 20 receives and thereby detects gamma rays (mainly peculiar gamma rays from radioactive nuclides in the imaging target TG). Every time the gamma ray detector 20 detects a gamma ray (mainly a peculiar gamma ray from a radioactive nuclide in the imaging target TG) incident on it, it outputs a gamma ray detection signal. The gamma ray detection signal indicates incidence of a gamma ray on the gamma ray detector 20, and in addition includes energy information E on the energy of the gamma ray incident on the gamma ray detector 20. Typically, when a gamma ray is incident on the gamma ray detector 20, a pulse-form voltage signal with a crest value commensurate with the energy of the gamma ray is output as the gamma ray detection signal.

The gamma ray detector 20 can be built with, for example, a semiconductor detector using Ge (germanium). In that case, the gamma ray detector 20 can detect the energy of a gamma ray with an energy resolution of about 0.2 to 0.5%.

Instead, the gamma ray detector 20 may be built with a semiconductor detector using any semiconductor material (for example, Si, CdTe, or CdZnTe) other than Ge. Instead, the gamma ray detector 20 may be built with a scintillation detector. Although scintillation detectors generally have lower energy resolutions than semiconductor detectors, it is possible to use one so long as it has an energy resolution sufficiently high to discriminate a target peculiar gamma ray.

———Imaging Processor———

The imaging processor 30 generates a distribution image of a target nuclide present in the imaging target TG based on a beta ray detection signal output from the beta ray detector 10 and a gamma ray detection signal output from the gamma ray detector 20. The target nuclide can be any nuclide that is present in the imaging target TG and that is taken as the target of imaging. For example, the target nuclide can be any particular type B nuclide present in the imaging target TG, or may be, in a case where the imaging target TG contains a type A nuclide and a type B nuclide, the combination of those type A and type B nuclides.

A distribution image of a target nuclide denotes an image that indicates the distribution of the target nuclide on a plane parallel to XY-plane. For example, an image obtained by projecting onto a predetermined projection plane parallel to XY-plane the location in the imaging target TG at which the target nuclide is present corresponds to a distributing image of the target nuclide. In a case where a drug labeled with a type A nuclide as a target nuclide (that is, a type A probe) is distributed in the imaging target TG, a distribution image of the target nuclide is a distribution image of the type A probe as well. Likewise, in a case where a drug labeled with a type B nuclide as a target nuclide (that is, a type B probe) is distributed in the imaging target TG, a distribution image of the target nuclide is a distribution image of the type B probe as well.

As shown in FIG. 5, the imaging processor 30 includes a coincident measurement checker 31 and an image reconstructor 32.

The coincident measurement checker 31 is fed with the output of the beta ray detector 10 and the output of the gamma ray detector 20. The coincident measurement checker 31 checks whether detection of a beta ray by the beta ray detector 10 and detection of a gamma ray by the gamma ray detector 20 coincide (in other words, whether a beta ray and a gamma ray are measured coincidentally), and outputs a coincident measurement check signal that indicates the result of the check. Here, the concept of coincidence allows for a predetermined time span: if the time difference between the time point of beta ray detection by the beta ray detector 10 and the time point of gamma ray detection by the gamma ray detector 20 is equal to or smaller than a predetermined value, those rays are judged to be measured coincidentally, and otherwise they are judged not to be measured coincidentally. This check is, in the following description, referred to as a coincident measurement check.

There are finite time differences among the time point $t_{\beta 1}$ at which a type A or type B nuclide in the imaging target TG emits a beta ray, the time point $t_{\beta 2}$ at which the beta ray interacts with the beta ray detector 10 inside it, the time point $t_{\beta 3}$ at which the beta ray detector 10 outputs a beta ray detection signal indicating the result of the detection, and the time point $t_{\beta 4}$ at which the beta ray detection signal is fed to the coincident measurement checker 31 (as time passes, time points $t_{\beta 1}$, $t_{\beta 2}$, $t_{\beta 3}$, and $t_{\beta 4}$ occur in this order). The time from time point $t_{\beta 1}$ to time point $t_{\beta 4}$ depends on the response of the detector 10, the length of the signal line from the detector 10, etc., and has a length that is peculiar to the beta ray detector system including the detector 10. Moreover, due to a difference in response time resulting from a difference in detection location, and due to signal noise, the time difference between the time point $t_{\beta 1}$ at which the beta ray is actually emitted and the time point $t_{\beta 4}$ at which the beta ray detection signal is fed to the coincident measurement checker 3 has a time spread. This spread of the time difference indicates the accuracy with which the time point of radiation emission can be determined, and is generally called time resolution.

Likewise, there are finite time differences among the time point $t_{\gamma 1}$ at which a type B nuclide in the imaging target TG actually emits a gamma ray (peculiar gamma ray), the time point $t_{\gamma 2}$ at which the gamma ray interacts with the gamma ray detector 20 inside it, the time point $t_{\gamma 3}$ at which the gamma ray detector 20 outputs a gamma ray detection signal indicating the result of the detection, and the time point $t_{\gamma 4}$ at which the gamma ray detection signal is fed to the coincident measurement checker 31 (as time passes, time points $t_{\gamma 1}$, $t_{\gamma 2}$, $t_{\gamma 3}$, $t_{\gamma 4}$ occur in this order). As in the beta ray detector system, the time difference between time points $t_{\gamma 1}$ and $t_{\gamma 4}$ has a length and a time resolution that are peculiar to the gamma ray detector system including the gamma ray detector 20.

So that the response time (the time from $t_{\beta 1}$ to $t_{\beta 4}$) of the beta ray detector system and the response time (the time from $t_{\gamma 1}$ to $t_{\gamma 4}$) of the gamma ray detector system are equal, a signal delay circuit is inserted in whichever of those detector systems has the shorter response time. This permits the coincident measurement checker 31 to regard the difference between the time point at which it is fed with a beta ray detection signal and the time point at which it is fed with a gamma ray detection signal as the difference between the time point of beta ray detection by the beta ray detector 10 and the time point of gamma ray detection by the gamma ray detector 20. With consideration given to the signal delay circuit, time points $t_{\beta 4}$ and $t_{\gamma 4}$ can be understood respectively as the time point of beta ray detection by the beta ray detector 10 (beta ray detector system) and the time point of gamma ray detection by the gamma ray detector 20 (gamma ray detector system). When fed with a beta ray detection signal from the beta ray detector 10, the coincident measurement checker 31 checks whether or not it, within a predetermined time $T_{TH}$ of the time point of that feeding, is then fed with a gamma ray detection signal from the gamma ray detector 20. If the check result is affirmative (that is, if a gamma ray is detected within the predetermined time $T_{TH}$ of the time point of detection of the beta ray), the coincident measurement checker 31 recognizes coincident measurement of a beta ray and a gamma ray (which may be a peculiar gamma ray), and outputs a coincident measurement check signal with the logic value "1"; otherwise, the coincident measurement checker 31 dismisses coincident measurement of a beta ray and a gamma ray (which may be a peculiar gamma ray), and outputs a coincident measurement check signal with the logic value "0".

There is a time difference after a beta ray is emitted until a peculiar gamma ray is emitted. Unless the excited state of the daughter nucleus has an especially long half-life, that time difference is of the order of femtoseconds to picoseconds, and is thus shorter than the time resolution of common radiation detectors. Also finite are the time of flight of a beta ray, the time of flight of a gamma ray, and the time after a positron is emitted until it is annihilated. These times are all sufficiently short compared with the time resolution of the detectors involved. Accordingly, the time $T_{TH}$ used in the coincident measurement check is determined mainly in accordance with the time resolutions of the beta ray detector 10 and the gamma ray detector 20 respectively. That is, with consideration given to the time spread of the accuracy with which the beta ray detector 10 determines the time point of detection of a beta ray and the time spread of the accuracy with which the gamma ray detector 20 determines the time point of detection of a gamma ray, the length of the time $T_{TH}$ is determined such that it allows for those time spreads.

Each instance of a beta ray being detected by the beta ray detector 10 is referred to as an event. For each event, the imaging processor 30 generates event data based on the output of the beta ray detector 10 and the output of the gamma ray detector 20.

Event data can be recorded to a memory incorporated in the imaging apparatus 1 (for example, a memory, unillustrated, incorporated in the imaging processor 30). It is efficient to check, as the sole condition (master trigger) under which to generate and record event data, whether the beta ray detector 10 detected radiation (a beta ray). In this case, when the gamma ray detector 20 alone detected radiation (a gamma ray), no event data are recorded. Considering that imaging is impossible based on information from the gamma ray detector 20 alone, it is efficient not to acquire needless data. However, in a case where the beta ray detector 10 and the gamma ray detector 20 are operated independently and the data from the two detectors (data that constitute event data) are marked with a common time stamp so that, after measurement, a coincident measurement check will be performed off line, detection of radiation by each of the detectors serves as a master trigger for the recording of event data.

One unit of event data in connection with one event includes location information (x, y) in the beta ray detection signal in connection with that event and the coincident measurement check signal in connection with the same event, and can additionally include energy information E in the gamma ray detection signal in connection with the same event.

With respect to one unit of event data in connection with one event, the location information (x, y) included in that event data indicates both the detection location of the beta ray by the beta ray detector 10 in the same event and the location of the nuclide that emitted the beta ray in the same event. These locations are, as mentioned previously, locations in the X- and Y-axis directions.

With respect to one unit of event data in connection with one event, the energy information E included in that event data indicates the energy of the gamma ray detected in connection with the same event.

Figure 9:
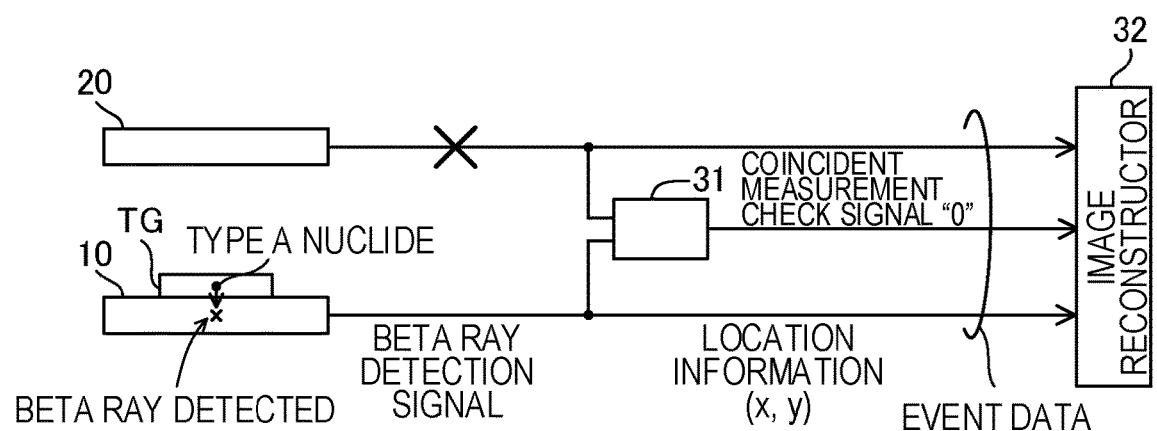
FIG. 9 is a diagram showing how signals behave when type A radioactive decay occurs in connection with an imaging apparatus according to an embodiment of the present invention.

FIG. 9 is a diagram illustrating an event resulting from beta decay of a type A nuclide (hereinafter referred to as a type A event). In a type A event, a type A nuclide emits a beta ray, with the result that a beta ray detection signal including location information (x, y) indicating the location of that type A nuclide is generated, but no peculiar gamma ray is emitted. Accordingly, the event data of a type A event include location information (x, y) and coincident measurement check information "0", and includes no energy information E. A beta ray resulting from beta decay of a type A nuclide may fail to be detected by the beta ray detector 10. Such an incidence, however, does not constitute an event (the same is true with a type B nuclide).

Figure 10A:
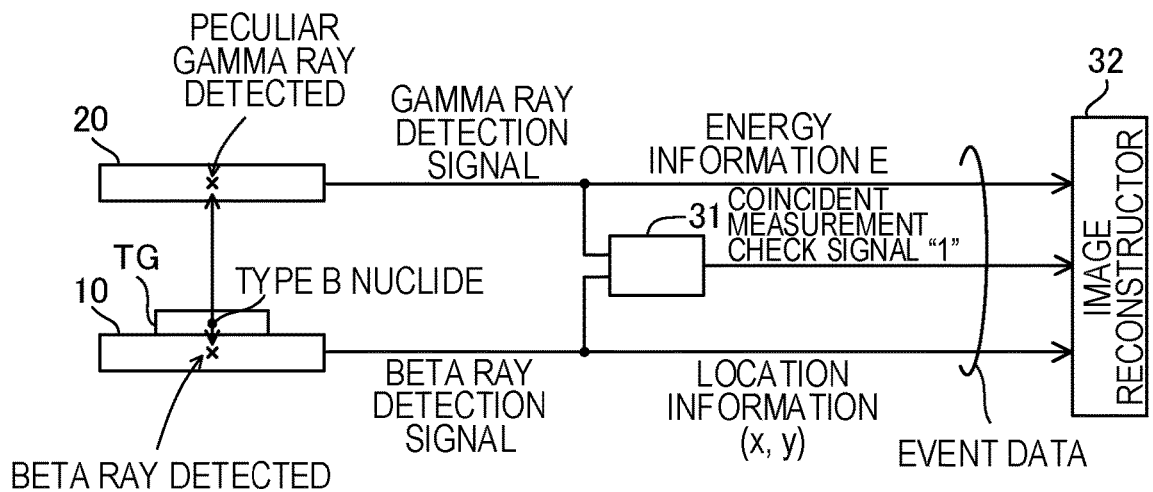
FIGS. 10A and 10B are each a diagram showing how signals behave when type B radioactive decay occurs in connection with an imaging apparatus according to an embodiment of the present invention.
Figure 10B:
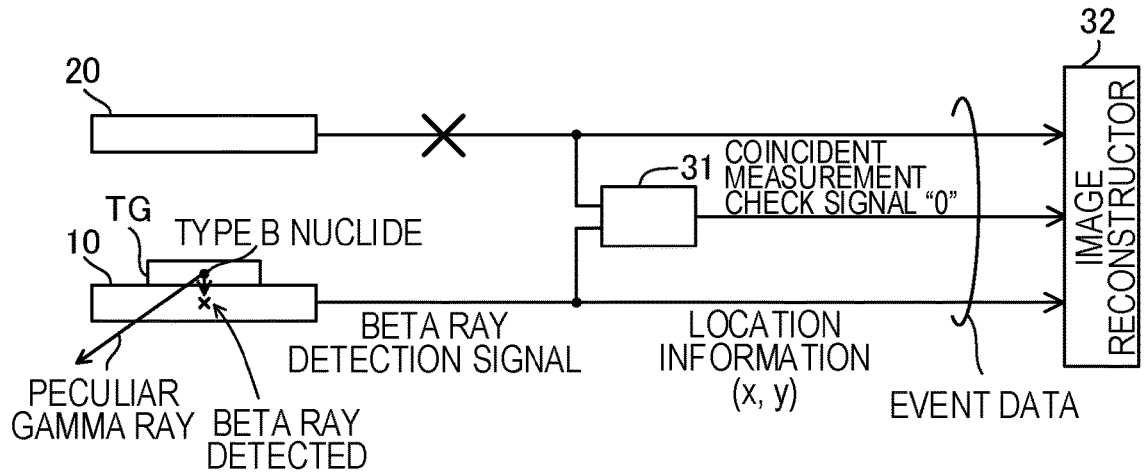

FIGS. 10A and 10B are diagrams each illustrating an event resulting from beta decay of a type B nuclide (hereinafter referred to as a type B event). In a type B event, a type B nuclide emits a beta ray, with the result that a beta ray detection signal including location information (x, y) indicating the location of that type B nuclide is generated; on the other hand, the type B nuclide can emit, subsequent to the beta ray, a peculiar gamma ray, with the result that a gamma ray detection signal can be generated. In a type B event, if, as shown in FIG. 10A, a peculiar gamma ray is incident on the gamma ray detector 20 and is detected by it, a gamma ray detection signal is generated. Thus, the event data include the location information (x, y) in the beta ray detection signal, coincident measurement check information "1", and the energy information E in the gamma ray detection signal. By contrast, in a B-type event, if, as shown in FIG. 10B, no peculiar gamma ray is incident on the gamma ray detector 20 and thus no peculiar gamma ray is detected by it, the event data includes location information (x, y) and coincident measurement check information "0", and includes no energy information E.

Increasing the solid angle of detection of a peculiar gamma ray in the gamma ray detector 20 leads to increasing the probability of detection of a peculiar gamma ray in a type B event. Accordingly, so that the solid angle will be increased, it is preferable to dispose the gamma ray detector 20 as close to the imaging target TG as possible, and to use a gamma ray detector 20 sufficiently large to cover the imaging target TG. With the imaging apparatus 1, it is possible to easily obtain a solid angle as large as $2\pi$ even as compared with the solid angle of detection of a peculiar gamma ray in a PET system as discussed in Patent Document 1 (Japanese Patent No. 5526435).

Figure 11:
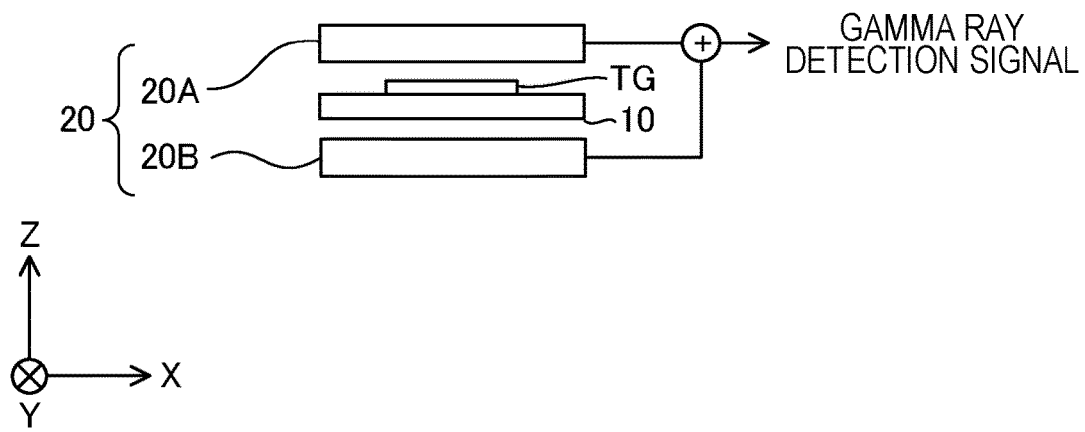
FIG. 11 is a diagram showing an example of the configuration of a gamma ray detector according to an embodiment of the present invention.

A plurality of gamma ray detectors may be used. For example, it is possible, as shown in FIG. 11, to build the gamma ray detector 20 with a gamma ray detector 20A disposed over the imaging target TG and a gamma ray detector 20B disposed under the imaging target TG, and thereby to further increase the above-mentioned solid angle. In that case, the imaging target TG and the beta ray detector 10 are disposed between the gamma ray detectors 20A and 20B. In the example shown in FIG. 11, the gamma ray detectors 20A and 20B constitute a single gamma ray detector 20, and the logical sum of the outputs of the gamma ray detectors 20A and 20B constitutes the output signal of the gamma ray detector 20. That is, the gamma ray detector 20 in FIG. 11 outputs a gamma ray detection signal when a gamma ray (which may be a peculiar gamma ray) is detected at either of the locations where the gamma ray detectors 20A and 20B are disposed respectively.

The image reconstructor 32 performs image reconstruction based on a plurality of units of image data, and thereby generates a distribution image of a target nuclide. In practice, the beta ray detection location information (x, y) included in the obtained event data is histogramed on the pixelated XY-plane, and thereby a distribution of radioactive intensity is obtained.

For convenience' sake, the configuration, operation, and other features of the imaging apparatus 1 described above will be referred to as the basic example. The following description discusses, by way of a plurality of examples, specific examples of the generated distribution image as well as more specific examples of the configuration, operation, application, and so forth of the imaging apparatus 1. Unless otherwise stated or unless inconsistent, any description of the basic example applies to the examples described below. For any description of the examples that contradicts that of the basic example, the description of the examples prevails. Unless inconsistent, any description of any one of the examples described below applies to any other of the examples (that is, any two or more of the examples may be combined together).

First Example

A first example will be described. In the first example, it is assumed that the imaging target TG contains a type B nuclide $NC_{B1}$ and a type B nuclide $NC_{B2}$, which are type B nuclides different from each other. The imaging target TG may also contain a type A nuclide, but here it is assumed that it contains no type A nuclide. The peculiar gamma rays of the type B nuclides $NC_{B1}$ and $NC_{B2}$ have energies $E_1$ and $E_2$ respectively, energies $E_1$ and $E_2$ being different from each other. The gamma ray detector 20 can detect gamma rays while resolving energies $E_1$ and $E_2$. That is, the gamma ray detector 20 can detect, while discriminating between, a peculiar gamma ray with energy $E_1$ and a peculiar gamma ray with energy $E_2$.

In the gamma ray detector 20, when a peculiar gamma ray emitted from the type B nuclide $NC_{B1}$ is detected, a gamma ray detection signal including energy information E (referred to also as energy information $E_1$) indicating that the detected peculiar gamma ray has energy $E_1$ is output; when a peculiar gamma ray emitted from the type B nuclide $NC_{B2}$ is detected, a gamma ray detection signal including energy information E (referred to also as energy information $E_2$) indicating that the detected peculiar gamma ray has energy $E_2$ is output. Thus, the output of a gamma ray detection signal including energy information $E_1$ indicates detection of a peculiar gamma ray from the type B nuclide $NC_{B1}$ in the gamma ray detector 20, and the output of a gamma ray detection signal including energy information $E_2$ indicates detection of a peculiar gamma ray from the type B nuclide $NC_{B2}$ in the gamma ray detector 20.

Figure 12:
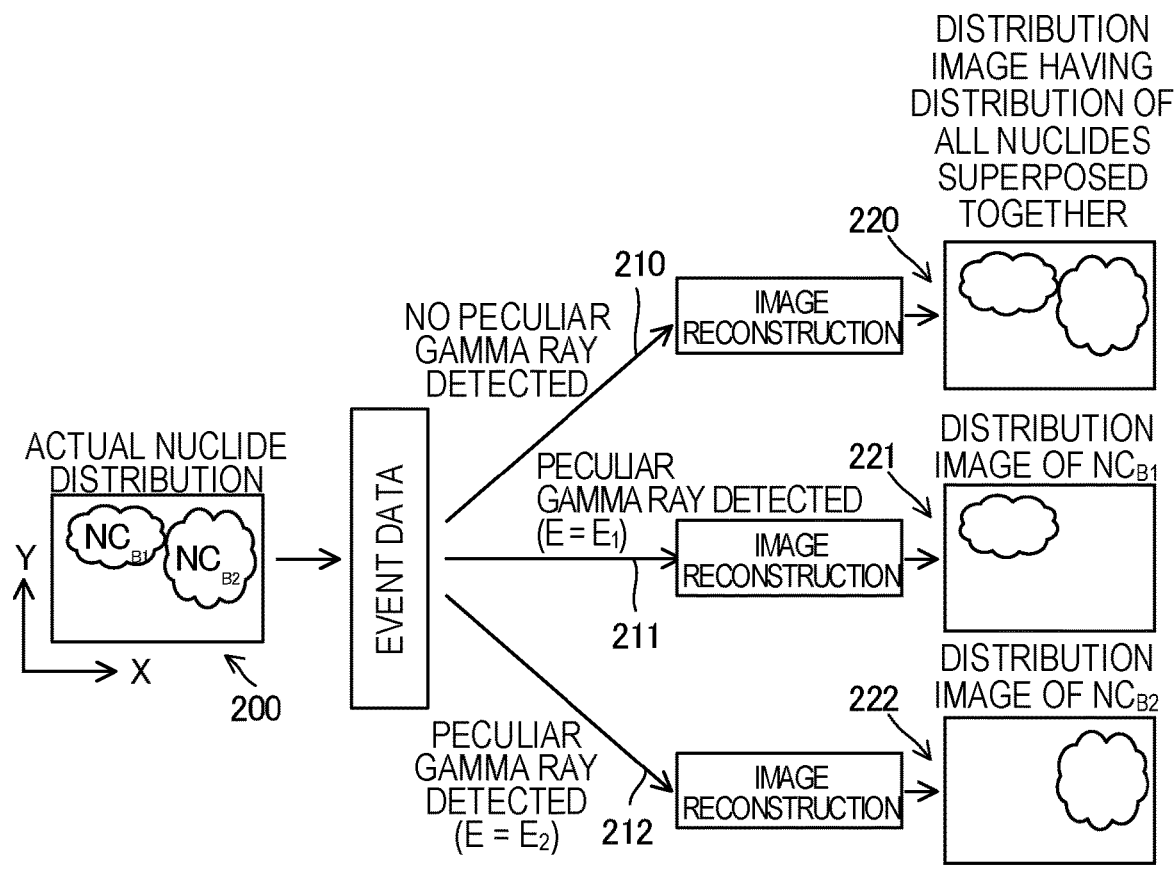
FIG. 12 is a conceptual diagram of image reconstruction according to a first example of the present invention.

FIG. 12 is a conceptual diagram of image reconstruction in the first example. An image 200 shows the actual distribution of the type B nuclides $NC_{B1}$ and $NC_{B2}$ in the imaging target TG. What is acquired in the first example are a group of event data 210 which is a collection of event data on events that are not accompanied by detection of a peculiar gamma ray, a group of event data 211 which is a collection of event data on events that are accompanied by detection of a peculiar gamma ray with energy $E_1$, and a group of event data 212 which is a collection of event data on events that are accompanied by detection of a peculiar gamma ray with energy $E_2$.

Event data on an event that is accompanied by detection of a peculiar gamma ray with energy $E_1$ are event data that include a coincident measurement check signal "1" and that in addition include location information (x, y) and energy information $E_1$. Event data on an event that is accompanied by detection of a peculiar gamma ray with energy $E_2$ are event data that include a coincident measurement check signal "1" and that in addition include location information (x, y) and energy information $E_2$.

Event data on an event that is not accompanied by detection of a peculiar gamma ray are event data on an event in which no peculiar gamma ray is detected in the gamma ray detector 20; they typically are event data that include a coincident measurement check signal "0" and that thus include location information (x, y) but no energy information E. As will be described later, annihilation or the like may cause a gamma ray other than a peculiar gamma ray to be incident on the gamma ray detector 20, in which case the coincident measurement check signal in the event data may indicate "1"; even then, if the energy information E in the same event data does not indicate energy $E_1$ or $E_2$, those event data are classified as event data on an event that is not accompanied by detection of a peculiar gamma ray.

When a beta ray from a nuclide that does not emit a peculiar gamma ray is detected, it can accidentally occur that a gamma ray with an energy equal to energy $E_1$ or $E_2$ is detected coincidentally. Such an incidence, called accidental coincident measurement, inevitably occurs on an apparatus that performs coincident measurement, though its frequency varies with the number of times of detection per unit time. Accidental coincident measurement that occurs on the imaging apparatus 1 can be corrected for by a method analogous to background elimination by well-known delay coincident measurement used in PET.

The location information (x, y) in each unit of event data in the group of event data 211 represents the detected values of the X- and Y-axis components of the presence location of the type B nuclide $NC_{B1}$ in the imaging target TG. Accordingly, the image reconstructor 32 can generate a distribution image 221 of the type B nuclide $NC_{B1}$ in the imaging target TG by histograming on XY-plane the location information (x, y) in every unit of event data in the group of event data 211.

Thus, the imaging processor 30 can generate a distribution image 221 of the type B nuclide $NC_{B1}$ by using the location information (x, y) acquired when the time difference between the time point of beta ray detection by the beta ray detector 10 and the time point of gamma ray detection by the gamma ray detector 20 is equal to or less than the predetermined time $T_{TH}$ (that is, the coincident measurement check signal indicates "1") and in addition energy information $E_1$ is obtained. In other words, the imaging processor 30 can generate a distribution image 221 of the type B nuclide $NC_{B1}$ by using the location information (x, y) in event data that indicate detection of a peculiar gamma ray with energy $E_1$ in the gamma ray detector 20 within the predetermined time $T_{TH}$ of the time point of beta ray detection by the beta ray detector 10.

The location information (x, y) in each unit of event data in the group of event data 212 represents the detected values of the X- and Y-axis components of the presence location of the type B nuclide $NC_{B2}$ in the imaging target TG. Accordingly, the image reconstructor 32 can generate a distribution image 222 of the type B nuclide $NC_{B2}$ in the imaging target TG by histograming on XY-plane the location information (x, y) in every unit of event data in the group of event data 212.

Thus, the imaging processor 30 can generate a distribution image 222 of the type B nuclide $NC_{B2}$ by using the location information (x, y) acquired when the time difference between the time point of beta ray detection by the beta ray detector 10 and the time point of gamma ray detection by the gamma ray detector 20 is equal to or less than the predetermined time $T_{TH}$ (that is, the coincident measurement check signal indicates "1") and in addition energy information $E_2$ is obtained. In other words, the imaging processor 30 can generate a distribution image 222 of the type B nuclide $NC_{B2}$ by using the location information (x, y) in event data that indicate detection of a peculiar gamma ray with energy $E_2$ in the gamma ray detector 20 within the predetermined time $T_{TH}$ of the time point of beta ray detection by the beta ray detector 10.

The location information (x, y) in each unit of event data in the group of event data 210 represents the detected values of the X- and Y-axis components of the presence location of either of the type B nuclides $NC_{B1}$ and $NC_{B2}$ in the imaging target TG. Accordingly, the image reconstructor 32 can generate a distribution image 220 that corresponds to the distribution of all the nuclides (here, type B nuclides $NC_{B1}$ and $NC_{B2}$) present in the imaging target TG in a form superposed on each other by histograming on XY-plane the location information (x, y) in every unit of event data in the group of event data 210. That is, the imaging processor 30 can generate a distribution image 220 by using the location information (x, y) in event data on events that are not accompanied by detection of a peculiar gamma ray.

As described above, with the imaging apparatus 1, it is possible to image the distribution of a plurality of type B nuclides at once in a manner discriminable from each other.

Though being capable of generating distribution images 220, 221, and 222, the imaging apparatus 1 may so operate as to generate only one of those distribution images (in particular, for example, a distribution image 221 or 222); it may so operate as to generate only two of those distribution images (in particular, for example, distribution images 221 and 222).

In a case where, as a beta ray, a positron is emitted from a type B nuclide, the positron first contributes to generation of scintillation light in the scintillator 11, and then the positron annihilates with an electron nearby. Then a gamma ray with an energy of 511 keV resulting from the annihilation may be incident on the gamma ray detector 20. Accordingly, in a case where a type B nuclide that emits a positron through beta decay is contained in the imaging target TG, so that a gamma ray resulting from annihilation may be distinguished from a peculiar gamma ray, it is preferable to use, as each type B nuclide contained in the imaging target TG, a type B nuclide of which the peculiar gamma ray has an energy other than 511 keV. It is preferable, moreover, to give the gamma ray detector 20 an energy resolution sufficient to resolve energy $E_1$, energy $E_2$, and 511 keV from each other. This applies also to the other examples described below.

As described above, with a nuclide that emits a positron through positive beta decay, when the positron is incident on the beta ray detector 10, it eventually annihilates to produce two gamma rays (annihilation gamma rays) with an energy of 511 keV each in opposite directions, that is, 180° apart from each other. Such an annihilation gamma ray may be detected by the gamma ray detector 20. When a nuclide that undergoes positive beta decay and a nuclide that undergoes negative beta decay are imaged simultaneously, it is possible to discriminate nuclides by checking for detection of an annihilation gamma ray. While this applies also to the other examples described below, the technique will be described in detail in connection with the seventh example.

On the other hand, when a beta ray is incident on the scintillator 11, a characteristic X-ray may be generated, and this characteristic X-ray may be incident on the gamma ray detector 20. A characteristic X-ray has an energy (about several kiloelectronvolts to one hundred and several tens of kiloelectronvolts) lower than that (for example, about 300 to 2000 keV) of a peculiar gamma ray. To prevent such a characteristic X-ray from being incident on the gamma ray detector 20, it is preferable that an absorber that absorbs X-rays, with low energies, be provided in front of the detector. This applies also to the other examples described below.

While the discussion above deals with a case where the imaging target TG contains two type B nuclides, the imaging target TG may contain three or more type B nuclides the peculiar gamma rays corresponding to which have different energies from each other. Also in that case, the imaging apparatus 1, while setting "0" or "1" in a coincident measurement check signal based on the time point of beta ray detection and the time point of gamma ray detection, generate event data every time an event takes place, and image the distribution of three or more type B nuclides at once in a manner discriminable from each other (the same applies also to the other examples described below).

More specifically, in a case where, in addition to the type B nuclides $NC_{B1}$ and $NC_{B2}$, a type B nuclide $NC_{B3}$ the peculiar gamma ray corresponding to which has an energy $E_3$ is contained in the imaging target TG, the imaging processor 30 can generate a distribution image 221 of the type B nuclide $NC_{B1}$ and a distribution image 222 of the type B nuclide $NC_{B2}$ as described above, and in addition can generate a distribution image (unillustrated) of the type B nuclide $NC_{B3}$ by using the location information (x, y) acquired when the time difference between the time point of beta ray detection by the beta ray detector 10 and the time point of gamma ray detection by the gamma ray detector 20 is equal to or less than the predetermined time $T_{TH}$ (that is, the coincident measurement check signal indicates "1") and in addition energy information E indicating $E_3$ is obtained.

Second Example

A second example will be described. In the second example, it is assumed that the imaging target TG contains a type A nuclide $NC_{A1}$ along with the type B nuclide $NC_{B1}$ discussed in connection with the first example, and that it contains no other nuclide. The gamma ray detector 20 can detect a peculiar gamma ray emitted from the type B nuclide $NC_{B1}$; that is, it can detect a peculiar gamma ray with energy $E_1$. In the gamma ray detector 20, when a peculiar gamma ray emitted from the type B nuclide $NC_{B1}$ is detected, a gamma ray detection signal including energy information E (energy information $E_1$) indicating that the detected peculiar gamma ray has energy $E_1$ is output. That is, the output of a gamma ray detection signal including energy information $E_1$ indicates detection of a peculiar gamma ray from the type B nuclide $NC_{B1}$ in the gamma ray detector 20.

Figure 13:
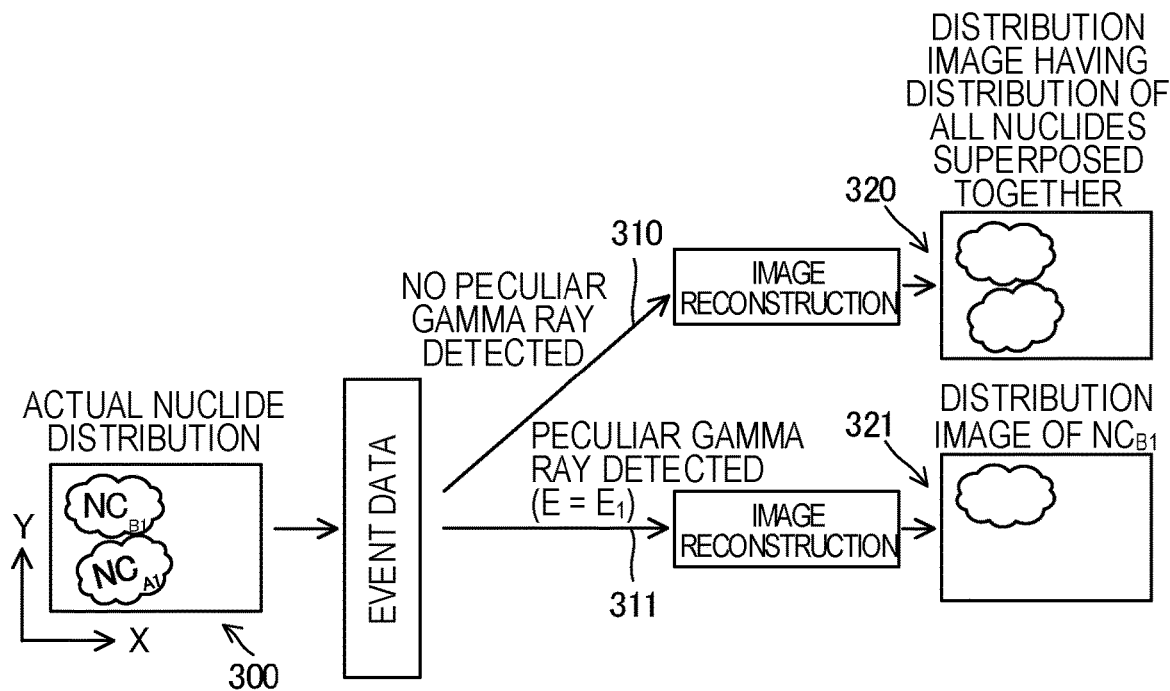
FIG. 13 is a conceptual diagram of image reconstruction according to a second example of the present invention.

FIG. 13 is a conceptual diagram of image reconstruction in the second example. An image 300 shows the actual distribution of the type A nuclide $NC_{A1}$ and the type B nuclide $NC_{B1}$ in the imaging target TG. In the second example, what is acquired are a group of event data 310 which is a collection of event data on events that are not accompanied by detection of a peculiar gamma ray and a group of event data 311 which is a collection of event data on events that are accompanied by detection of a peculiar gamma ray with energy $E_1$.

Event data on an event that is accompanied by detection of a peculiar gamma ray with energy $E_1$ are event data that include a coincident measurement check signal "1" and that in addition include location information (x, y) and energy information $E_1$.

Event data on an event that is not accompanied by detection of a peculiar gamma ray are event data on an event in which no peculiar gamma ray is detected in the gamma ray detector 20; they typically are event data that include a coincident measurement check signal "0" and that thus include location information (x, y) but no energy information E. As mentioned in connection with the first example, annihilation or the like may cause a gamma ray other than a peculiar gamma ray to be incident on the gamma ray detector 20, in which case the coincident measurement check signal in the event data may indicate "1"; even then, if the energy information E in the same event data does not indicate energy $E_1$, those event data are classified as event data on an event that is not accompanied by detection of a peculiar gamma ray.

The location information (x, y) in each unit of event data in the group of event data 311 represents the X- and Y-axis components of the presence location of the type B nuclide $NC_{B1}$ in the imaging target TG. Thus, the image reconstructor 32 can generate a distribution image 321 of the type B nuclide $NC_{B1}$ in the imaging target TG by histograming on XY-plane the location information (x, y) in every unit of event data in the group of event data 311.

That is, the imaging processor 30 can generate a distribution image 321 of the type B nuclide $NC_{B1}$ by using the location information (x, y) acquired when the time difference between the time point of beta ray detection by the beta ray detector 10 and the time point of gamma ray detection by the gamma ray detector 20 is equal to or less than the predetermined time $T_{TH}$ (that is, the coincident measurement check signal indicates "1") and in addition the energy information $E_1$ is obtained. In other words, the imaging processor 30 can generate a distribution image 321 of the type B nuclide $NC_{B1}$ by using the location information (x, y) in event data that indicate detection of a peculiar gamma ray with energy $E_1$ in the gamma ray detector 20 within the predetermined time $T_{TH}$ of the time point of beta ray detection by the beta ray detector 10.

In the second example, the type B nuclide $NC_{B1}$ is the only nuclide that emits a peculiar gamma ray; thus, each event is of one of the two types: one in which a peculiar gamma ray is detected or one in which no peculiar gamma ray is detected. Accordingly, the gamma ray detector 20 has only to check whether or not a peculiar gamma ray is detected. Then, the imaging processor 30 can generate a distribution image 321 of the type B nuclide $NC_{B1}$ by using the location information (x, y) of events in which the time difference between the time point of beta ray detection by the beta ray detector 10 and the time point of gamma ray detection by the gamma ray detector 20 is equal to or less than the predetermined time $T_{TH}$ (that is, the coincident measurement check signal indicates "1") and in addition a peculiar gamma ray is detected.

The location information (x, y) in each unit of event data in the group of event data 310 represents the detected values of the X- and Y-axis components of the presence location of either of the type A nuclide $NC_{A1}$ and the type B nuclide $NC_{B1}$ in the imaging target TG. Accordingly, the image reconstructor 32 can generate a distribution image 320 that corresponds to the distribution of all the nuclides (here, nuclides $NC_{A1}$ and $NC_{B1}$) present in the imaging target TG superposed on each other by histograming on XY-plane the location information (x, y) in every event data in the group of event data 310. That is, the imaging processor 30 can generate a distribution image 320 by using the location information (x, y) in event data on events that are not accompanied by detection of a peculiar gamma ray. In other words, the imaging processor 30 can generate a distribution image 320 by using the location information (x, y) in event data that indicate no detection of a peculiar gamma ray (here, a peculiar gamma ray with energy $E_1$) in the gamma ray detector 20 within the predetermined time $T_{TH}$ of the time point of beta ray detection by the beta ray detector 10.

As described above, with the imaging apparatus 1, in a case where the imaging target TG contains both a type A nuclide and a type B nuclide, it is possible to image the distribution of only the type B nuclide in an extracted manner, and simultaneously to image also the distribution of the type A and type B nuclides in a superposed manner.

It is also possible, by synthesizing distribution images 320 and 321 together, to generate a distribution image (hereinafter referred to as a type A distribution image) that shows the distribution of only the type A nuclide $NC_{A1}$. In the synthesizing process, the pixel value (the luminance value at a pixel) at a location of interest on the type A distribution image is given by "$P_{320}-((1-\varepsilon)/\varepsilon)P_{321}$". Here, $P_{320}$ represents the pixel value at the location of interest on the distribution image 320, $P_{321}$ represents the pixel value at the location of interest on the distribution image 321, and $\varepsilon$ represents the detection efficiency for the energy of the peculiar gamma ray emitted from the nuclide in the imaging target TG.

Though being capable of generating distribution images 320 and 321 and a type A distribution image, the imaging apparatus 1 may so operate as to generate only one of those distribution images (in particular, for example, only a distribution image 321); it may so operate as to generate only two of those distribution images (in particular, for example, a distribution image 321 and a type A distribution image).

The gamma ray detector 20 in the second example has only to check for the presence of a peculiar gamma ray with energy $E_1$; thus, unlike in a case where a plurality of peculiar gamma rays with mutually different energies have to be detected in a manner that permits discrimination among them as in the first example, the energy resolution required in the gamma ray detector 20 can be low.

A supplementary description of the detection efficiency $\varepsilon$ will now be given. The detection efficiency $\varepsilon$ with respect to a peculiar gamma ray on the gamma ray detector 20 has a value that depends on energy. Moreover, the detection efficiency $\varepsilon$ on the gamma ray detector 20 varies from place to place, and thus, if we disregard the thickness of the imaging target TG in the Z-axis direction and consider the imaging target TG to be a two-dimensional object, the detection efficiency $\varepsilon$ is a function of a two-dimensional location (x, y). The detection efficiency $\varepsilon$ with respect to a peculiar gamma ray at location (x, y) for a given energy will be represented by $\varepsilon(x, y)$.

Also the beta ray detector 10 has a detection efficiency that depends on location, and quantification of radioactivity on it requires correction to be performed on an image obtained by histograming the number of times of detection at each location. The image data so obtained is here assumed to be corrected with the location-dependent detection efficiency (the same applies to the examples other than this one).

In a case where the imaging target TG contains a type A nuclide and a type B nuclide, if the actual two-dimensional distribution of the type A and type B nuclides in the imaging target TG are represented, each as a function of location (x, y), by A(x, y) and B(x, y) respectively, then an image accompanied by detection of a peculiar gamma ray is represented by "$\varepsilon(x, y) B(x, y)$", and an image not accompanied by detection of a peculiar gamma ray is represented by "$A(x, y)+(1-\varepsilon(x, y)) B(x, y)$". Here, it is assumed that the probability of each nuclide in the imaging target TG emitting a beta ray and the probability of the type B nuclide in the imaging target TG emitting, subsequently to a beta, a peculiar gamma ray are both one.

Accordingly, if an image accompanied by coincident detection of a beta ray and a peculiar gamma ray (in this example, an image generated from the group of event data 311) is represented by T(x, y) and an image not accompanied by detection of a peculiar gamma ray (in this example, an image generated from the group of event data 310) is represented by D(x, y), the actual distribution of the type B nuclide in the imaging target TG is given by "$B(x, y)=T(x, y)/\varepsilon(x, y)$". By subtracting one image from the other, it is possible to obtain the actual distribution of the type A nuclide in the imaging target TG, and the actual distribution of the type A nuclide in the imaging target TG is given by "$A(x, y)=D(x, y)-T(x, y) (1-\varepsilon(x, y))/\varepsilon(x, y)$". Actual measurement gives D(x, y) and T(x, y), and thus, with consideration given to the detection efficiency $\varepsilon(x, y)$, according to the above formula, B(x, y) and A(x, y) can be obtained respectively as a distribution image of the type B nuclide (in this example, a distribution image 321) and a distribution image of the type A nuclide (a type A distribution image). This method of deriving a distribution image of each nuclide with consideration given to detection efficiency is applicable equally to any of the examples other than this one.

Third Example

A third example will be described. In the third example, it is assumed that the imaging target TG contains the type A nuclide $NC_{A1}$ and the type B nuclides $NC_{B1}$ and $NC_{B2}$, all discussed in connection with the first or second examples. As mentioned in connection with the first example, the peculiar gamma rays of the type B nuclides $NC_{B1}$ and $NC_{B2}$ have energies $E_1$ and $E_2$ respectively, which differ from each other. The gamma ray detector 20 can detect gamma rays while resolving energies $E_1$ and $E_2$. That is, the gamma ray detector 20 can detect, while discriminating between, a peculiar gamma ray with energy $E_1$ and a peculiar gamma ray with energy $E_2$.

In the gamma ray detector 20, when a peculiar gamma ray emitted from the type B nuclide $NC_{B1}$ is detected, a gamma ray detection signal including energy information E (energy information $E_1$) indicating that the detected peculiar gamma ray has energy $E_1$ is output, and when a peculiar gamma ray emitted from the type B nuclide $NC_{B2}$ is detected, a gamma ray detection signal including energy information E (energy information $E_2$) indicating that the detected peculiar gamma ray has energy $E_2$ is output. That is, the output of a gamma ray detection signal including energy information $E_1$ indicates detection of a peculiar gamma ray from the type B nuclide $NC_{B1}$ in the gamma ray detector 20, and the output of a gamma ray detection signal including energy information $E_2$ indicates detection of a peculiar gamma ray from the type B nuclide $NC_{B2}$ in the gamma ray detector 20.

Figure 14:
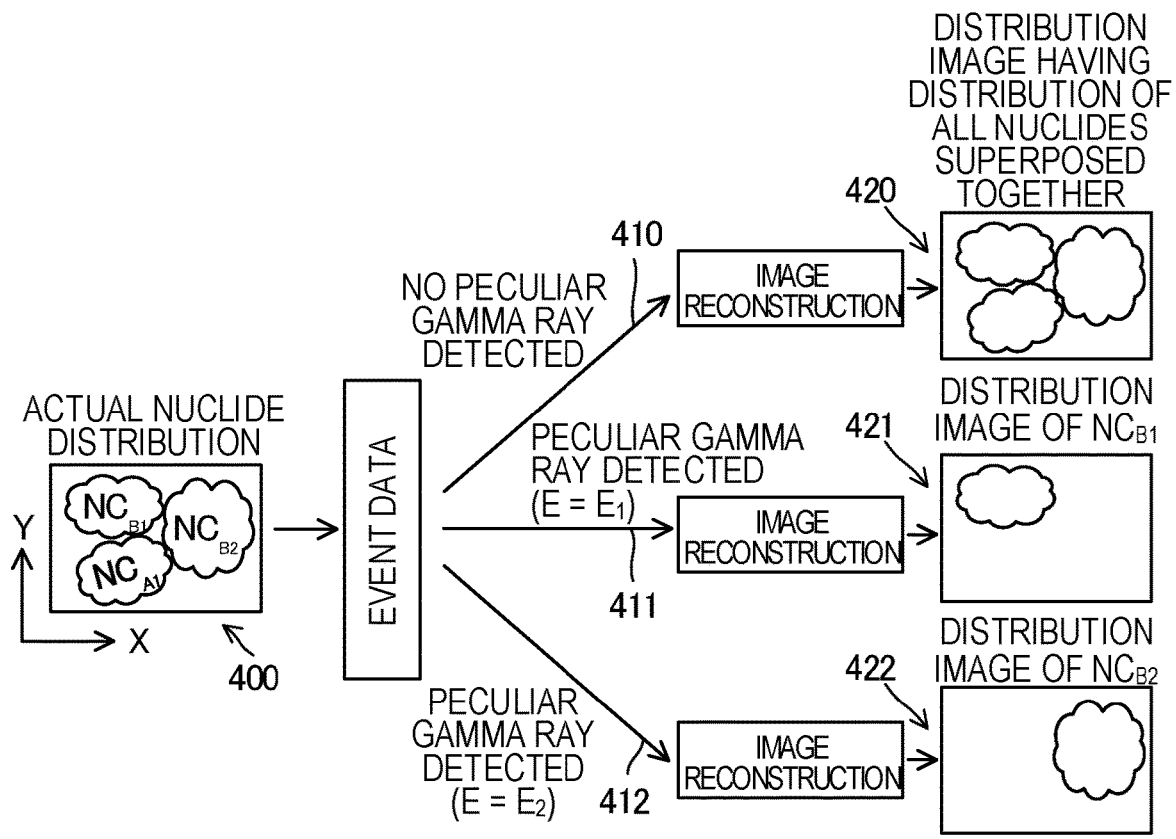
FIG. 14 is a conceptual diagram of image reconstruction according to a third example of the present invention.

FIG. 14 is a conceptual diagram of image reconstruction in the third example. An image 400 shows the actual distribution of the type A nuclide $NC_{A1}$ and the type B nuclides $NC_{B1}$ and $NC_{B2}$ in the imaging target TG. In the third example, what is acquired are a group of event data 410 which is a collection of event data on events that are not accompanied by detection of a peculiar gamma ray, a group of event data 411 which is a collection of event data on events that are accompanied by detection of a peculiar gamma ray with energy $E_1$, and a group of event data 412 which is a collection of event data on events that are accompanied by detection of a peculiar gamma ray with energy $E_2$.

Event data on an event that is accompanied by detection of a peculiar gamma ray with energy $E_1$ are event data that include a coincident measurement check signal "1" and that in addition include location information (x, y) and energy information $E_1$. Event data on an event that is accompanied by detection of a peculiar gamma ray with energy $E_2$ are event data that include a coincident measurement check signal "1" and that in addition include location information (x, y) and energy information $E_2$.

Event data on an event that is not accompanied by detection of a peculiar gamma ray are event data on an event in which no peculiar gamma ray is detected in the gamma ray detector 20; they typically are event data that include a coincident measurement check signal "0" and that thus include location information (x, y) but no energy information E. As mentioned in connection with the first example, annihilation or the like may cause a gamma ray other than a peculiar gamma ray to be incident on the gamma ray detector 20, in which case the coincident measurement check signal in the event data may indicate "1"; even then, if the energy information E in the same event data does not indicate energy $E_1$ or $E_2$, those event data are classified as event data on an event that is not accompanied by detection of a peculiar gamma ray.

The location information (x, y) in each unit of event data in the group of event data 411 represents the X- and Y-axis components of the presence location of the type B nuclide $NC_{B1}$ in the imaging target TG. Thus, the image reconstructor 32 can generate a distribution image 421 of the type B nuclide $NC_{B1}$ in the imaging target TG by histograming on XY-plane the location information (x, y) in every unit of event data in the group of event data 411.

That is, the imaging processor 30 can generate a distribution image 421 of the type B nuclide $NC_{B1}$ by using the location information (x, y) acquired when the time difference between the time point of beta ray detection by the beta ray detector 10 and the time point of gamma ray detection by the gamma ray detector 20 is equal to or less than the predetermined time $T_{TH}$ (that is, the coincident measurement check signal indicates "1") and in addition the energy information $E_1$ is obtained. In other words, the imaging processor 30 can generate a distribution image 421 of the type B nuclide $NC_{B1}$ by using the location information (x, y) in event data that indicate detection of a peculiar gamma ray with energy $E_1$ in the gamma ray detector 20 within the predetermined time $T_{TH}$ of the time point of beta ray detection by the beta ray detector 10.

The location information (x, y) in each unit of event data in the group of event data 412 represents the X- and Y-axis components of the presence location of the type B nuclide $NC_{B2}$ in the imaging target TG. Thus, the image reconstructor 32 can generate a distribution image 422 of the type B nuclide $NC_{B2}$ in the imaging target TG by histograming on XY-plane the location information (x, y) in every unit of event data in the group of event data 412.

That is, the imaging processor 30 can generate a distribution image 422 of the type B nuclide $NC_{B2}$ by using the location information (x, y) acquired when the time difference between the time point of beta ray detection by the beta ray detector 10 and the time point of gamma ray detection by the gamma ray detector 20 is equal to or less than the predetermined time $T_{TH}$ (that is, the coincident measurement check signal indicates "1") and in addition the energy $E_2$ is obtained. In other words, the imaging processor 30 can generate a distribution image 422 of the type B nuclide $NC_{B2}$ by using the location information (x, y) in event data that indicate detection of a peculiar gamma ray with energy $E_2$ in the gamma ray detector 20 within the predetermined time $T_{TH}$ of the time point of beta ray detection by the beta ray detector 10.

The location information (x, y) in each unit of event data in the group of event data 410 represents the detected values of the X- and Y-axis components of the presence location of one of the nuclides $NC_{A1}$, $NC_{B1}$, and $NC_{B2}$ in the imaging target TG. Accordingly, the image reconstructor 32 can generate a distribution image 420 that corresponds to the distribution of all the nuclides (here, nuclides $NC_{A1}$, $NC_{B1}$, and $NC_{B2}$) present in the imaging target TG superposed on each other by histograming on XY-plane the location information (x, y) in every event data in the group of event data 410. That is, the imaging processor 30 can generate a distribution image 420 by using the location information (x, y) in event data on events that are not accompanied by detection of a peculiar gamma ray. In other words, the imaging processor 30 can generate a distribution image 420 by using the location information (x, y) in event data that indicate no detection of either a peculiar gamma ray with energy $E_1$ or a peculiar gamma ray with energy $E_2$ in the gamma ray detector 20 within the predetermined time $T_{TH}$ of the time point of beta ray detection by the beta ray detector 10.

As described above, with the imaging apparatus 1, it is possible to image the distribution of a plurality of type B nuclides at once in a manner discriminable from each other, and simultaneously to image the distribution of type A and type B nuclides in a form superposed on each other. Moreover, by synthesizing distribution images 420 to 422 together by a method similar to the one described in connection with the second example, it is possible also to generate a distribution image that shows the distribution of only the type A nuclide $NC_{A1}$ (a type A distribution image).

Though being capable of generating distribution images 420 to 422 and a type A distribution image, the imaging apparatus 1 may so operate as to generate only one of those distribution images (in particular, for example, only a distribution image 421 or 422); it may so operate as to generate only two of those distribution images (in particular, for example, distribution image 421 and 422, or a distribution image 421 and a type A distribution image, or a distribution image 422 and a type A distribution image); it may so operate as to generate only three of those distribution images (in particular, for example, distribution image 421 and 422 and a type A distribution image).

This is particularly useful, for example, when radioactivation analysis as will be described later is performed in a case where, while a plurality of different radioactivated nuclides are generated in an imaging target TG, only a particular type B nuclide that emits a peculiar gamma ray needs to be imaged in an extracted manner based on the results of detection of the energy of the peculiar gamma ray.

As mentioned in connection with the first example, the imaging target TG may contain three or more type B nuclides the peculiar gamma rays corresponding to which have different energies from each other. The imaging target TG may even contain two or more type A nuclides.

Fourth Example

A fourth example will be described. The fourth example deals with an example of the use of the imaging apparatus 1.

In drug development, when studies are made on the behavior of a drug in terms of where in the living body it tends to concentrate, it is common to start at the cell level (with cells cultured on a flat surface such as a petri dish). The imaging apparatus 1 can be used in such studies.

Figure 15:
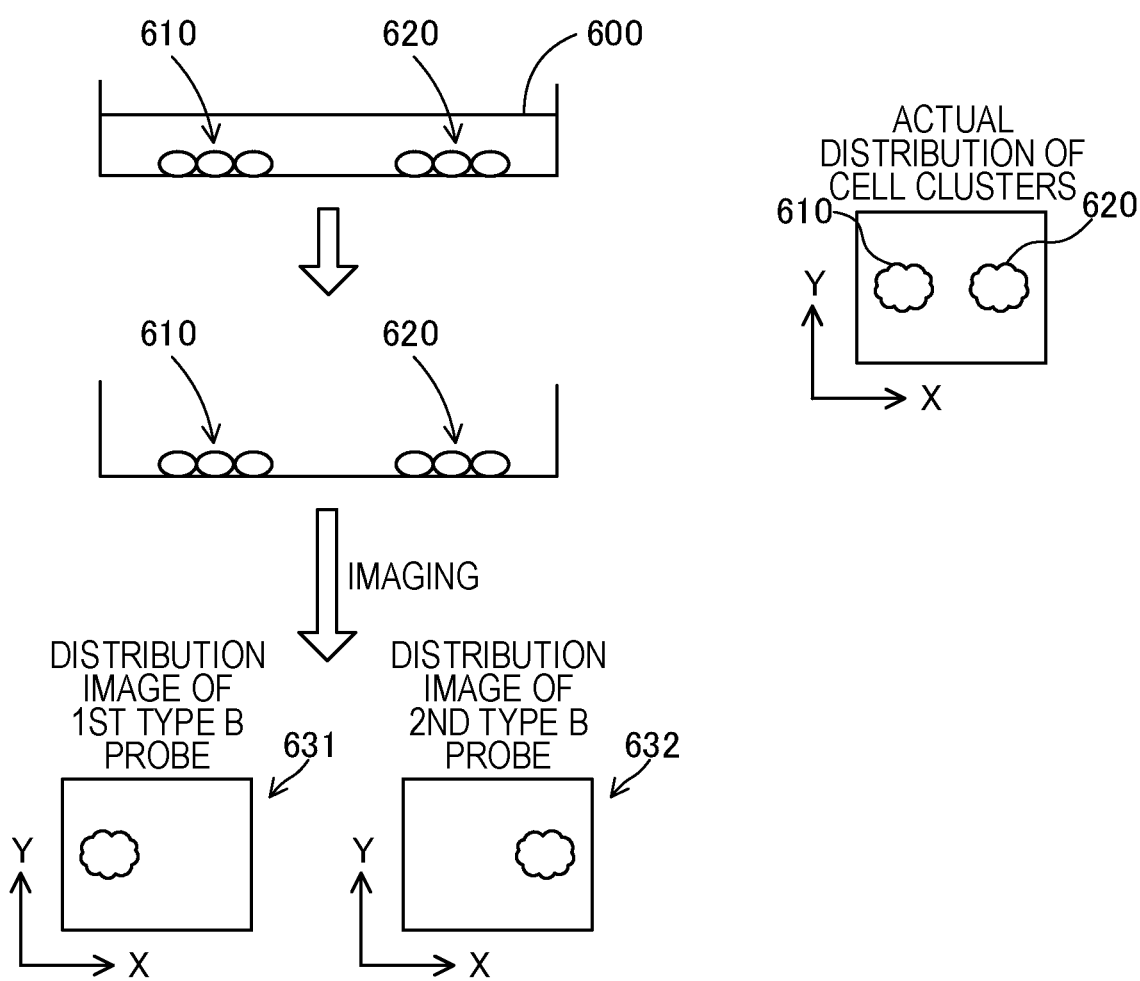
FIG. 15 is a diagram illustrating an example of the use of an imaging apparatus according to a fourth example of the present invention.

For example, as shown in FIG. 15, in a preparatory process, a first cluster 610 of cells which is a collection of first cells with a particular property and a second cluster 620 of cells which is a collection of second cells with another particular property are dipped for a predetermined length of time in a culture fluid 600 containing a first type B probe labeled with the type B nuclide $NC_{B1}$ and a second type B probe labeled with the type B nuclide $NC_{B2}$. This is expected to result in the first or second type B probe being ingested by either the first or second cells.

After the preparatory process described above, the culture fluid 600 is removed from the test vessel containing the culture fluid 600 and the first and second clusters 610 and 620 of cells, to obtain an imaging target TG, which is then subjected to imaging on the imaging apparatus 1. This yields a distribution image 631 of the first type B probe, which is a distribution image of the type B nuclide $NC_{B1}$, and a distribution image 632 of the second type B probe, which is a distribution image of the type B nuclide $NC_{B2}$. From the distribution images 631 and 632, it is possible to know which of the first and second cells more easily ingest the first type B probe and which of the first and second cells more easily ingest the second type B probe. For example, if it is possible to read, from the distribution images 631 and 632, that the first type B probe concentrates where the first cluster 610 of cells is present in the test vessel and that the second type B probe concentrates where the second cluster 620 of cells is present in the test vessel, then it is possible to know that, of the first and second cells, the first cells more easily ingest the first type B probe and the second cells more easily ingest the second type B probe.

The imaging apparatus 1 is useful also at the animal experiment level. For example, a mouse is administered, intravenously or orally, a first type B probe labeled with the type B nuclide $NC_{B1}$, a second type B probe labeled with the type B nuclide $NC_{B2}$, and a type A probe labeled with the type A nuclide $NC_{A1}$; a predetermined length of time thereafter, the mouse is dissected to prepare tissue sections (tissue sections with a thickness of, for example, about 50 μm) of the mouse. Using these tissue sections as the imaging target TG, by the method described in connection with the third example, distribution images 420 to 422 as shown in FIG. 14 are obtained with respect to the tissue sections. By referring to the distribution images 420 to 422 (and also a type A distribution image), it is possible to know which nuclide tends to concentrate in what part of the mouse. For example, in a case where cancerous cells are present in a particular part of the liver of the mouse, by preparing tissue sections of the mouse liver and subjecting them to imaging, it is possible to obtain information such as that only the first type B probe concentrates in the mouse liver or that only the second type B probe concentrates in the particular part of the mouse liver.

With living tissues so thin as to be regarded as a two-dimensional object, it may be possible, without sectioning them, to image them as an imaging target TG.

Fifth Example

A fifth example will be described. The fifth example deals with another example of the use of the imaging apparatus 1.

The imaging target TG of the imaging apparatus 1 is not limited to a living body. A plant can be taken as an imaging target TG, or an inorganic material can be taken as an imaging target TG.

For example, consider a case where, with respect to a battery (electrochemical cell) that contains sodium and iron, one wants to know the distribution of sodium or iron in an electrode film in the battery. Then, in a preparatory process, part of the sodium (stable isotope $^{23}$Na) contained in the battery is replaced with $^{22}$Na, which is a radioactive isotope of sodium, and part of the iron (stable isotope $^{56}$Fe) contained in the battery is replaced with $^{52}$Fe, which is a radioactive isotope of iron. Thereafter, the battery is subjected, as necessary, to a predetermined deterioration test, and then the electrode film of the battery is taken as an imaging target TG. In this case, $^{22}$Na and $^{52}$Fe function as type B nuclides $NC_{B1}$ and $NC_{B2}$ respectively.

Then, by the method described in connection with the first example, distribution images 220 to 222 are obtained (see FIG. 12), and from the distribution images 221 and 222, it is possible to know individually the distribution of sodium and that of iron in the electrode film of the battery.

Here are some other examples. It is possible to radioactivate, by irradiation with a beam from an accelerator, a trace metal or the like that has accumulated in a thin film such as an ion exchange membrane, and to take the thin film containing the radioactivated trace metal or the like as an imaging target TG. It is possible to take an ion-doped object as an imaging target TG. The present invention can be employed not only to obtain distribution images but also to perform particle tracking, in which a probe nuclide with a given amount of radioactivity is introduced into a single cell and is observed as a point of which the movement is tracked.

Sixth Example

A sixth example will be described. While the examples of use dealt with in the fourth and fifth examples belong to tracer analysis, in which a radioactive isotope as a tracer is added to an imaging target TG and how the tracer distributes in the imaging target TG is analyzed, the imaging apparatus 1 can be employed also in radioactivation analysis.

For example, with respect to the battery discussed in the fifth example, the battery's electrode film in a state containing neither a radioactive isotope of sodium nor a radioactive isotope of iron is irradiated with a high-energy gamma ray by use of an accelerator. This causes, in the battery's electrode film, some elements to undergo nuclear transformation and produce radioactive isotopes. The electrode film in this state, where radioactive isotopes have been produced, is taken as an imaging target TG. Then, for example, if the imaging target TG contains $^{22}$Na and $^{52}$Fe, these function as the type B nuclides $NC_{B1}$ and $NC_{B2}$ respectively; thus, by the method described in connection with the first example, distribution images 220 to 222 are obtained (see FIG. 12), and from the distribution images 221 and 222, it is possible to know individually the distribution of sodium and that of iron in the electrode film of the battery.

Seventh Example

A seventh example will be described. When a positron emitted by positive beta decay is incident on the beta ray detector 10, the positron loses energy to the beta ray detector 10; eventually it comes almost to rest and annihilates with an electron nearby (an electron inside the beta ray detector 10). The annihilation produces two gamma rays (annihilation gamma rays) with an energy of 511 keV each in opposite directions, that is, 180° apart from each other. By coincidentally measuring these annihilation gamma rays along with the positron on the detectors 10 and 20, it is possible to identify positive beta decay. That is, with an imaging target TG that contains both a nuclide that undergoes positive beta decay (hereinafter referred to as a positive beta decay nuclide) and a nuclide that undergoes negative beta decay (hereinafter referred to as a negative beta decay nuclide), it is possible to identify them in a discriminated manner according to whether or not annihilation gamma rays are detected. This method will now be elaborated on.

The gamma ray detector 20 is placed at a location where it can receive the annihilation gamma rays resulting from the annihilation of a positron from a positive beta decay nuclide with an electron inside the beta ray detector 10. By receiving a gamma ray (here, mainly an annihilation gamma ray), the gamma ray detector 20 detects the gamma ray. Every time the gamma ray detector 20 detects a gamma ray (here, mainly an annihilation gamma ray) incident on it, it outputs a gamma ray detection signal. As mentioned above, the gamma ray detection signal indicates incidence of a gamma ray on the gamma ray detector 20, and in addition includes energy information E indicating the energy of the incident gamma ray. When a gamma ray to be detected in the gamma ray detector 20 is an annihilation gamma ray, the time points $t_{\gamma 1}$ and $t_{\gamma 2}$ mentioned previously in connection with the response time of the gamma ray detection system (the time span from $t_{\gamma 1}$ to $t_{\gamma 4}$) are understood as, respectively, the time point at which the annihilation gamma ray is produced and the time point at which the annihilation gamma ray interacts with the gamma ray detector 20.

When fed with a beta ray detection signal from the beta ray detector 10, the coincident measurement checker 31 checks whether or not it, within a predetermined time $T_{TH}$ of the time point of that feeding, is then fed with a gamma ray detection signal from the gamma ray detector 20. If the check result is affirmative (that is, if a gamma ray is detected within the predetermined time $T_{TH}$ of the time point of detection of the beta ray), the coincident measurement checker 31 recognizes coincident measurement of a beta ray and a gamma ray (here, mainly an annihilation gamma ray), and outputs a coincident measurement check signal with the logic value "1"; otherwise, the coincident measurement checker 31 dismisses coincident measurement of a beta ray and a gamma ray (here, mainly an annihilation gamma ray), and outputs a coincident measurement check signal with the logic value "0".

Figure 16:
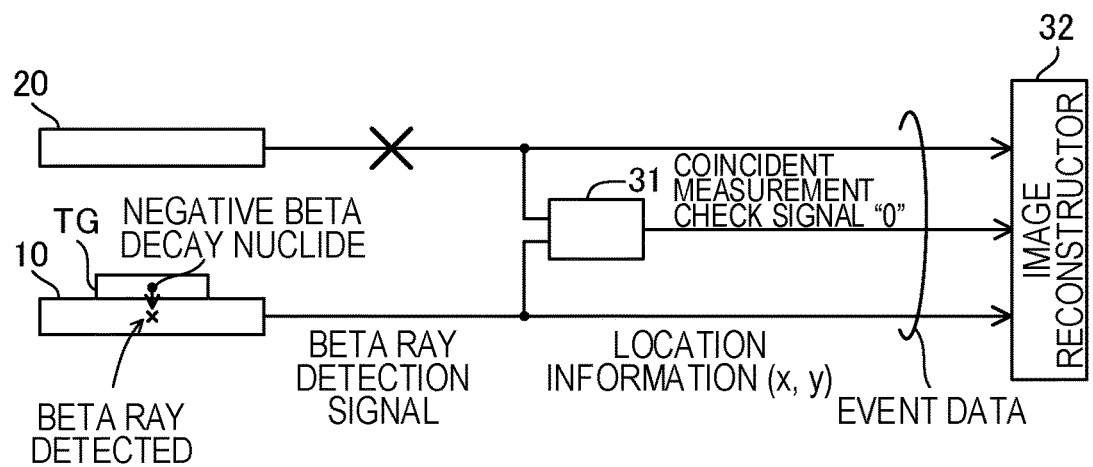
FIG. 16 is a diagram showing how signals behave when negative beta decay occurs in connection with an imaging apparatus according to a seventh example of the present invention.

FIG. 16 is a diagram illustrating an event that involves negative beta decay (hereinafter referred to as a negative beta decay event). In a negative beta decay event, a negative beta decay nuclide emits an electron as a beta ray, and a beta ray detection signal including location information (x, y) indicating the location of that beta decay nuclide is generated, but no annihilation gamma rays are produced. Accordingly, the event data on a negative beta decay event includes location information (x, y) and coincident measurement check information "0" but no energy information E. A beta ray from a negative beta decay nuclide may fail to be detected in the beta ray detector 10, and such an incidence does not constitute an event (the same is true with a positive beta decay nuclide).

Figure 17A:
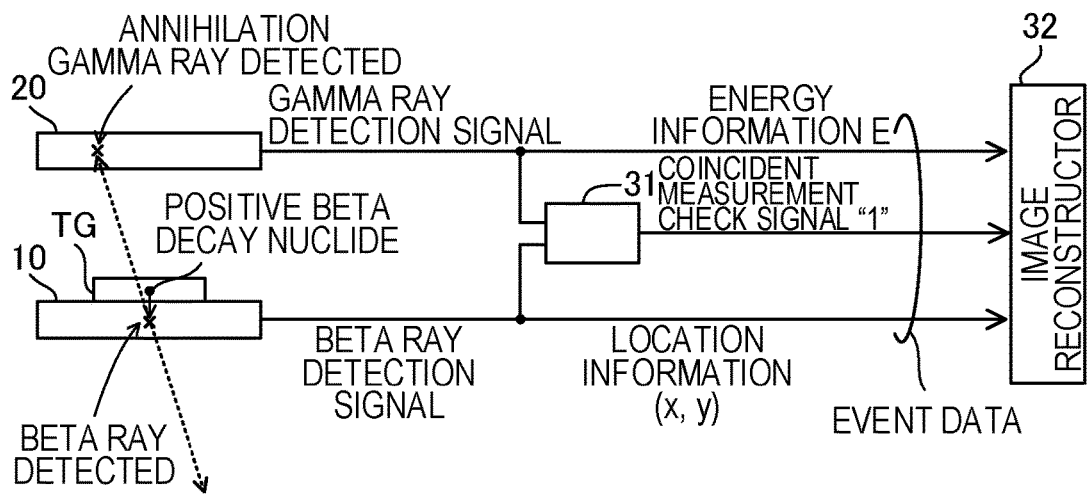
FIGS. 17A and 17B are each a diagram showing how signals behave when positive beta decay occurs in connection with an imaging apparatus according to the seventh example of the present invention.
Figure 17B:
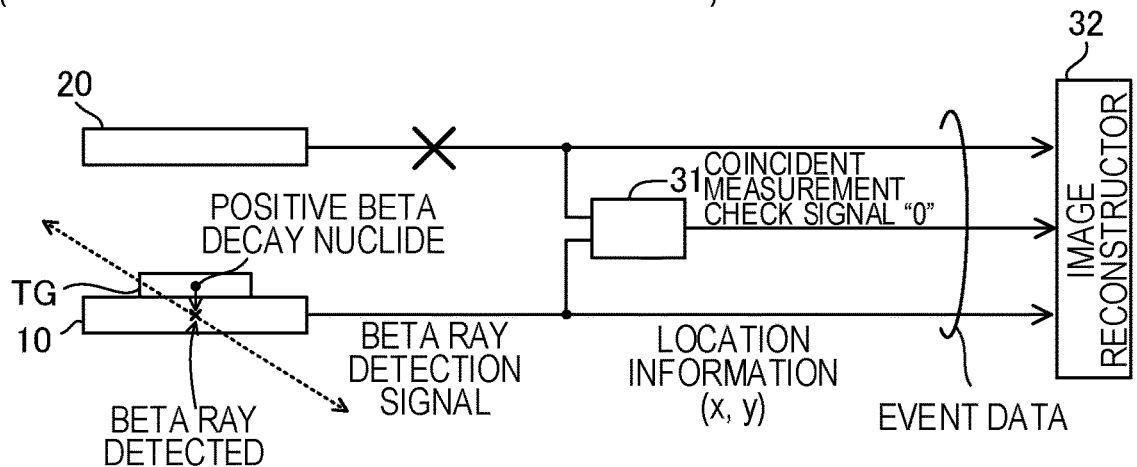

FIGS. 17A and 17B are diagrams each illustrating an event that involves positive beta decay (hereinafter referred to as a positive beta decay event). In FIGS. 17A and 17B, two arrowed broken line segments that extend in mutually opposite directions from near a beta ray detection location represent a pair of annihilation gamma rays. In a positive beta decay event, a positive beta decay nuclide emits a positron as a beta ray, and a beta ray detection signal including location information (x, y) indicating the location of the beta decay nuclide is generated; on the other hand, an annihilation gamma ray resulting from annihilation of the positron from the positive beta decay nuclide with an electron inside the beta ray detector 10 may be detected in the gamma ray detector 20, and thus a gamma ray detection signal may be generated. In a positive beta decay event, if, as shown in FIG. 17A, an annihilation gamma ray is incident on the gamma ray detector 20 and is detected, a gamma ray detection signal is generated; thus, the event data includes the location information (x, y) in the beta ray detection signal, coincident measurement check information "1", and the energy information E in the gamma ray detection signal. By contrast, in a positive beta decay event, if, as shown in FIG. 17B, no annihilation gamma ray is incident on the gamma ray detector 20, no annihilation gamma ray is detected; thus, the event data includes location information (x, y) and coincident measurement check information "0" but no energy information E.

Annihilation produces a pair of annihilation gamma rays that travel in mutually opposite directions. Here, however, it is assumed that a gamma ray detector 20 is arranged only over the imaging target TG so that, of the pair of annihilation gamma rays, only one annihilation gamma ray can be detected in the gamma ray detector 20. Instead, as shown in FIG. 11, gamma ray detectors may be arranged both over and under the imaging target TG, and only when a pair of annihilation gamma rays is detected in both of the gamma ray detectors coincidentally, it can be judged that annihilation gamma rays have been detected.

When, as a gamma ray, an annihilation gamma ray is detected in the gamma ray detector 20, a gamma ray detection signal including energy information E indicating that the energy of the detected gamma ray equals the energy of an annihilation gamma ray (511 keV) (hereinafter occasionally referred to also as energy information $E_{511}$) is output. That is, the output of a gamma ray detection signal including energy information $E_{511}$ indicates detection of an annihilation gamma ray in the gamma ray detector 20.

Figure 18:
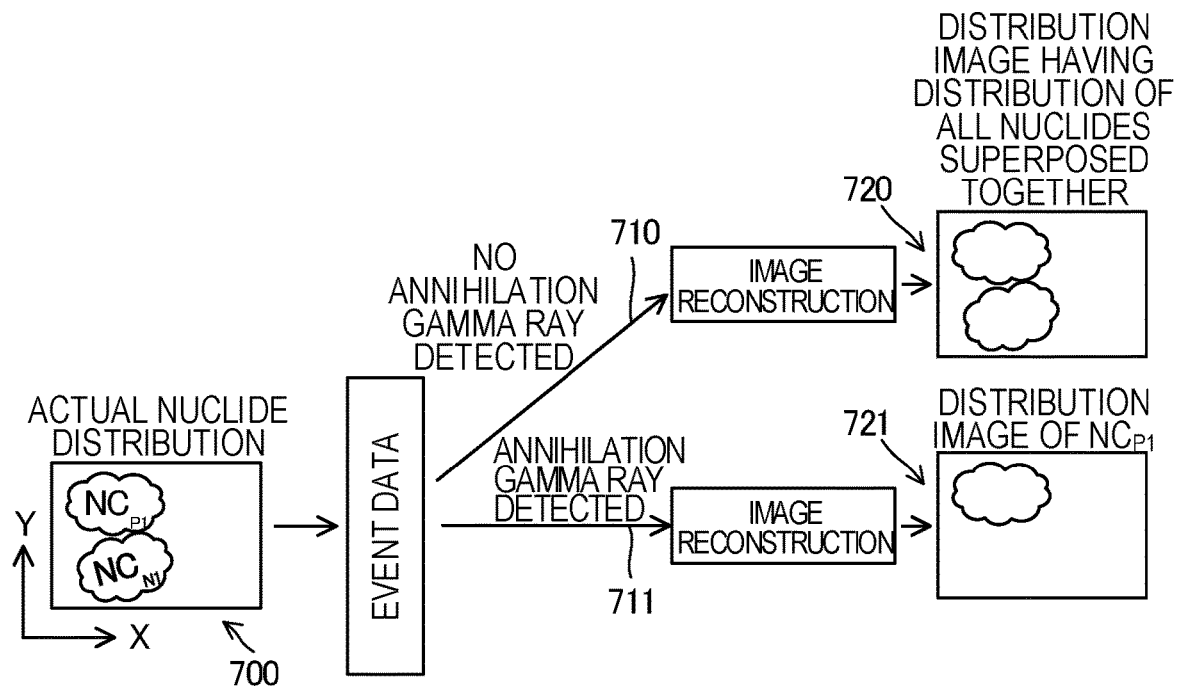
FIG. 18 is a conceptual diagram of image reconstruction according to the seventh example of the present invention.

FIG. 18 is a conceptual diagram of image reconstruction in the seventh example. Here, it is assumed that the imaging target TG contains a positive beta decay nuclide $NC_{P1}$ and a negative beta decay nuclide $NC_{N1}$. Then, the targets to be detected by the beta ray detector 10 are a beta ray as a positron emitted from the positive beta decay nuclide $NC_{P1}$ and a beta ray as an electron emitted from the negative beta decay nuclide $NC_{N1}$. The mode of radioactive decay of each of the nuclides $NC_{P1}$ and $NC_{N1}$ may be either of type A or of type B.

An image 700 shows the actual distribution of the positive beta decay nuclide $NC_{P1}$ and the negative beta decay nuclide $NC_{N1}$ in the imaging target TG. In the seventh example, acquired are a group of event data 710 which is a collection of the event data on events that are not accompanied by detection of an annihilation gamma ray and a group of event data 711 which is a collection of the event data on events that are accompanied by detection of an annihilation gamma ray.

Event data on an event that is accompanied by detection of an annihilation gamma ray are event data that include a coincident measurement check signal "1" and that in addition include location information (x, y) and energy information $E_{511}$.

Event data on an event that is not accompanied by detection of an annihilation gamma ray are event data on an event in which no annihilation gamma ray is detected in the gamma ray detector 20; they typically are event data that include a coincident measurement check signal "0", and thus include location information (x, y) but no energy information E. A gamma ray other than an annihilation gamma ray may be incident on the gamma ray detector 20, and in that case, the coincident measurement check signal in the event data may indicate "1". Even then, if the energy information E in the event data does not indicate energy $E_{511}$, those event data are classified as event data on an event that is not accompanied by detection of an annihilation gamma ray.

The location information (x, y) in each unit of event data in the group of event data 711 represents the detected value of the X- and Y-axis components of the presence location of the positive beta decay nuclide $NC_{P1}$ in the imaging target TG. Accordingly, the image reconstructor 32 can generate a distribution image 721 of the positive beta decay nuclide $NC_{P1}$ in the imaging target TG by histograming on XY-plane the location information (x, y) in every event data in the group of event data 711.

That is, the imaging processor 30 can generate a distribution image 721 of the positive beta decay nuclide $NC_{P1}$ by using the location information (x, y) acquired when the time difference between the time point of beta ray detection by the beta ray detector 10 and the time point of gamma ray detection by the gamma ray detector 20 is equal to or less than the predetermined time $T_{TH}$ (that is, the coincident measurement check signal indicates "1") and in addition energy information $E_{511}$ is obtained. In other words, the imaging processor 30 can generate a distribution image 721 of the positive beta decay nuclide $NC_{P1}$ by using the location information (x, y) in event data that indicate detection of an annihilation gamma ray in the gamma ray detector 20 within the predetermined time $T_{TH}$ of the time point of beta ray detection by the beta ray detector 10.

In the seventh example, the positive beta decay nuclide $NC_{P1}$ is the only nuclide that emits a positron; thus, each event is of one of the two types: one in which an annihilation gamma ray is detected or one in which no annihilation gamma ray is detected. Accordingly, the gamma ray detector 20 has only to check whether or not an annihilation gamma ray is detected.

The location information (x, y) in each unit of event data in the group of event data 710 represents the detected values of the X- and Y-axis components of the presence location of either of the negative beta decay nuclide $NC_{N1}$ and the positive beta decay nuclide $NC_{P1}$ in the imaging target TG. Accordingly, the image reconstructor 32 can generate a distribution image 720 that corresponds to the distribution of all the nuclides (here, nuclides $NC_{P1}$ and $NC_{N1}$) present in the imaging target TG superposed on each other by histograming on XY-plane the location information (x, y) in every unit of event data in the group of event data 710. That is, the imaging processor 30 can generate a distribution image 720 by using the location information (x, y) in event data on events that are not accompanied by detection of an annihilation gamma ray. In other words, the imaging processor 30 can generate a distribution image 720 by using the location information (x, y) in event data that indicate no detection of an annihilation gamma ray (here, an annihilation gamma ray with energy $E_1$) in the gamma ray detector 20 within the predetermined time $T_{TH}$ of the time point of beta ray detection by the beta ray detector 10.

As described above, with the imaging apparatus 1, in a case where the imaging target TG contains both a negative beta decay nuclide and a positive beta decay nuclide, it is possible to image only the positive beta decay nuclide in an extracted manner, and simultaneously to image the distribution of the negative and positive beta decay nuclides in a superposed manner.

Moreover, by synthesizing distribution images 720 and 721 together, it is possible to generate also a distribution image that shows the distribution of only the negative beta decay nuclide $NC_{N1}$ (hereinafter referred to as a negative beta decay nuclide distribution image). In the synthesizing process, the pixel value (the luminance value at a pixel) at a location of interest on the negative beta decay nuclide distribution image is given by "$P_{720} - ((1-\varepsilon')/\varepsilon') P_{721}$". Here, $P_{720}$ represents the pixel value at the location of interest on the distribution image 720, $P_{721}$ represents the pixel value at the location of interest on the distribution image 721, and $\varepsilon'$ represents the detection efficiency for the energy of the annihilation gamma ray. In reality, the detection efficiency $\varepsilon'$ has a value that depends on the location at which the annihilation gamma ray is produced; here, however, it is assumed that correction has been made for the dependence on location. The method for driving a distribution image of each nuclide with consideration given to detection efficiency is as described previously.

Though being capable of generating distribution images 720 and 721 and a negative beta decay nuclide distribution image, the imaging apparatus 1 may so operate as to generate only one of those distribution images (in particular, for example, a distribution image 721); or it may so operate as to generate only two of those distribution images (in particular, a distribution image 721 and a negative beta decay nuclide distribution image).

The method described in connection with this example may be combined with any of the other examples. For example, consider a case where the type B nuclide $NC_{B1}$ that emits a peculiar gamma ray with energy $E_1$ and the type B nuclide $NC_{B2}$ that emits a peculiar gamma ray with energy $E_2$, both discussed in the first example, are negative beta decay nuclides, and the negative beta decay nuclides $NC_{B1}$ and $NC_{B2}$ are along with a positive beta decay nuclide $NC_{P1}$ added to an imaging target TG. Then, the beta decay nuclides $NC_{B1}$ and $NC_{B2}$ can be identified based on the energies of their respective peculiar gamma rays. Moreover, since the negative beta decay nuclides $NC_{B1}$ and $NC_{B2}$ do not emit a positron, the positive beta decay nuclide $NC_{P1}$ can be identified through coincident measurement of an annihilation gamma ray and a beta ray by the method described in connection with this example. Thus, based on a beta ray detection signal from the imaging apparatus 10 and a gamma ray detection signal from the gamma ray detector 20, it is possible, from event data on events that are accompanied by detection of a peculiar gamma ray with energy $E_1$, event data on events that are accompanied by detection of a peculiar gamma ray with energy $E_2$, and event data on events that are accompanied by detection of an annihilation gamma ray, to generate individually a distribution image of the type B and negative beta decay nuclide $NC_{B1}$, a distribution image of the type B and negative beta decay nuclide $NC_{B2}$, and a distribution image of the positive beta decay nuclide $NC_{P1}$.

Eighth Example

An eighth example will be described. While methods for imaging a plurality of nuclides in a discriminable manner on the imaging apparatus 1 have been described, the imaging apparatus 1 is useful also in the imaging of a singe nuclide. This will now be described.

In the eighth example, it is assumed that the imaging target TG contains the type B nuclide $NC_{B1}$ discussed above. The imaging target TG may further contain, other than the type B nuclide $NC_{B1}$, a type B nuclide (for example, the type B nuclide $NC_{B2}$) or a type A nuclide; however, it is here assumed that the imaging target TG contains no nuclide other than the type B nuclide $NC_{B1}$. As mentioned previously, the energy of the peculiar gamma ray of the type B nuclide $NC_{B1}$ is represented by $E_1$.

Figure 19A:
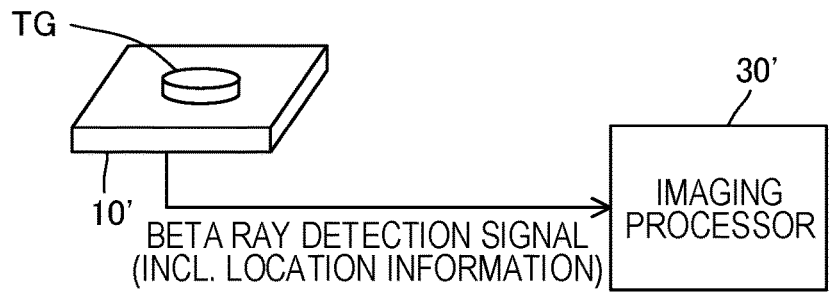
FIGS. 19A and 19B are, respectively, a diagram showing the configuration of a reference imaging apparatus and a conceptual diagram of image reconstruction, both according to an eighth example of the present invention.

Prior to a description of a method for the imaging of the type B nuclide $NC_{B1}$ on the imaging apparatus 1, a description will be given of a reference imaging apparatus with which the imaging apparatus 1 will be compared. As shown in FIG. 19A, the reference imaging apparatus is provided with a beta ray detector 10' and an imaging processor 30', the latter receiving a beta ray detection signal from the beta ray detector 10', but is not provided with a gamma ray detector 20. The beta ray detector 10' is the same detector as the beta ray detector 10 described previously, but the beta ray detector provided in the reference imaging apparatus is identified by the reference sign 10' for clear distinction from the beta ray detector 10 provided in the imaging apparatus 1 according to the embodiment. Radiation from the type B nuclide $NC_{B1}$ present in the imaging target TG is incident on the beta ray detector 10'.

Figure 19B:
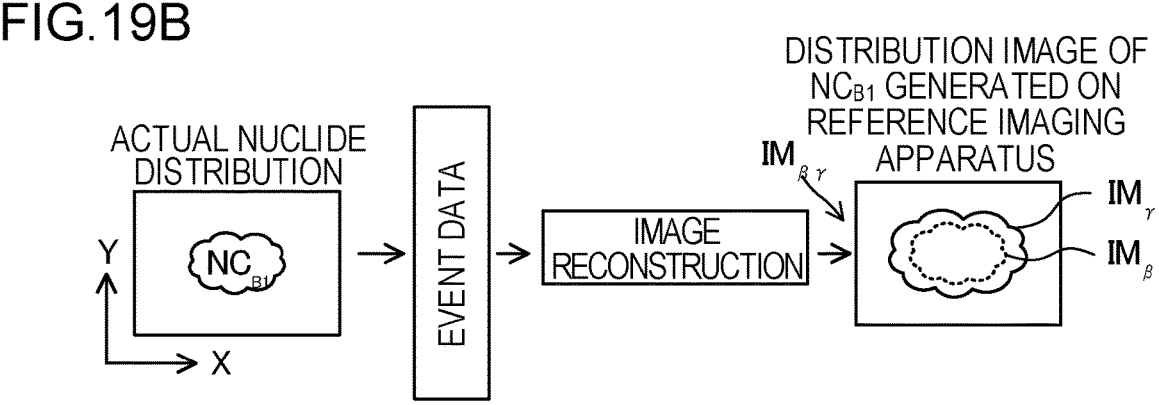

Although the beta ray detector 10' is intended to detect a beta ray as radiation, a gamma ray from the type B nuclide $NC_{B1}$ may interact with the beta ray detector 10', and also in that case, the beta ray detector 10' detects radiation (the same applies to the beta ray detector 10). However, the beta ray detector 10' cannot discriminate two kinds of radiation (beta and gamma rays), and thus, in reality, location information on a detected beta ray and location information on a detected gamma ray are mixed in a form undiscriminable from each other in the beta ray detection signal output from the beta ray detector 10' (the same applies to the beta ray detector 10). Thus, on the reference imaging apparatus, if image reconstruction is performed in the imaging processor 30' based on a beta ray detection signal from the beta ray detector 10', as shown in FIG. 19B, an image $IM_{\beta\gamma}$ as if showing the detected beta and gamma rays in a superposed manner is generated as a distribution image of the type B nuclide $NC_{B1}$.

The mage $IM_{\beta\gamma}$ is an image having an image $IM_{\beta}$ resulting from beta ray detection and an image $IM_{\gamma}$ resulting from gamma ray detection superposed on each other. Generally, the gamma ray has a longer flying range than the beta ray, and thus the image $IM_{\gamma}$ resulting from gamma ray detection turns out to be spread over a wider range than the actual distribution of the nuclide $NC_{B1}$ (that is, the image $IM_{\beta}$) (thus resulting in lower resolution).

Sufficiently reducing the thickness of the scintillation detector constituting the beta ray detector 10' permits most gamma rays to pass through the scintillation detector (that is, most gamma rays are not detected in the beta ray detector 10'), and this helps obtain an image close to the image $IM_{\beta}$. However, reducing the thickness of the scintillation detector leads to lower beta-ray detection efficiency, and thus it cannot be done beyond a certain limit. Even if the thickness of the scintillation detector is reduced down to the limit, it is not possible to completely eliminate detection of gamma rays in the beta ray detector 10'.

On the other hand, the imaging apparatus 1 according to the embodiment can, by use of the gamma ray detector 20, generate a distribution image of the nuclide $NC_{B1}$ with higher resolution than the reference imaging apparatus. The operation of the imaging apparatus 1 of the eighth example will now be described. As already mentioned, the gamma ray detector 20 can detect the peculiar gamma ray emitted from the type B nuclide $NC_{B1}$. That is, it can detect a peculiar gamma ray with energy $E_1$. When a peculiar gamma ray emitted from the type B nuclide $NC_{B1}$ is detected in the gamma ray detector 20, a gamma ray detection signal including energy information E indicating that the energy of the detected peculiar gamma ray equals energy $E_1$ (that is, energy information $E_1$) is output. That is, the output of a gamma ray detection signal including energy information $E_1$ indicates detection of a peculiar gamma ray from the type B nuclide $NC_{B1}$ in the gamma ray detector 20.

Figure 20:
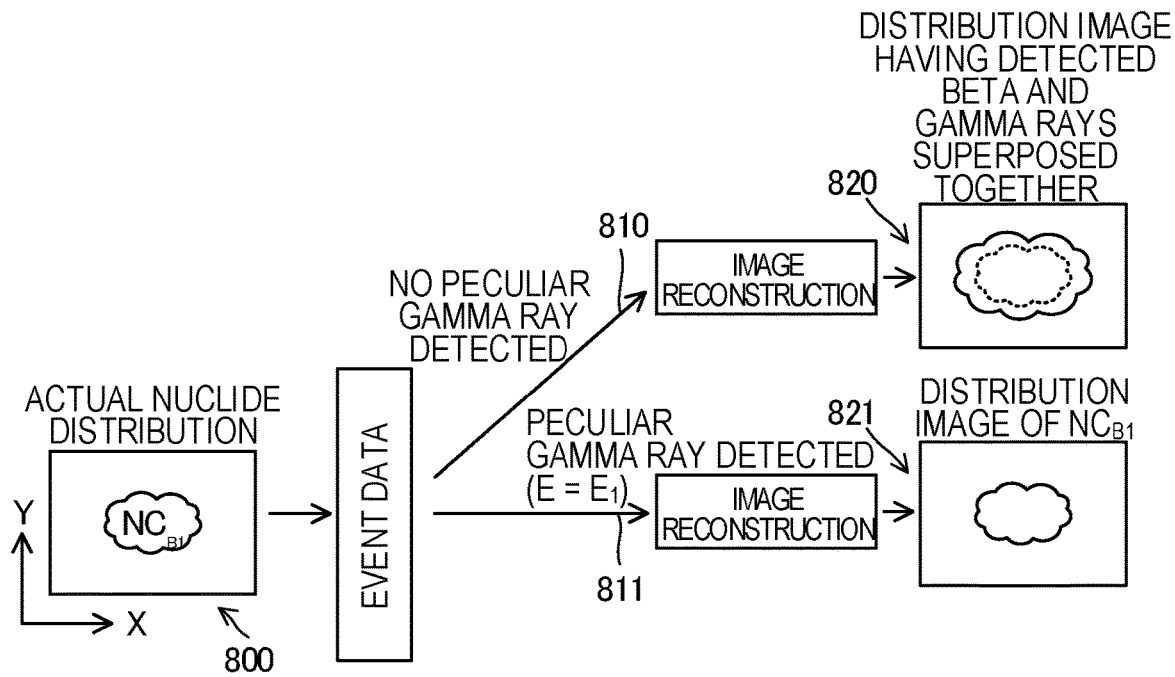
FIG. 20 is a conceptual diagram of image reconstruction according to the eighth example of the present invention.

FIG. 20 is a conceptual diagram of image reconstruction in the eighth example. An image 800 shows the actual distribution of the type B nuclide $NC_{B1}$ in the imaging target TG. In the eighth example, acquired are a group of event data 810 which is a collection of event data on events that are not accompanied by detection of a peculiar gamma ray and a group of event data 811 which is a collection of event data on events that are accompanied by detection of a peculiar gamma ray with energy $E_1$.

Event data on an event that is accompanied by detection of a peculiar gamma ray with energy $E_1$ are event data that include a coincident measurement check signal "1", and in addition are event data that include location information (x, y) and energy information $E_1$.

Event data on an event that is not accompanied by detection of a peculiar gamma ray are event data on an event in which no peculiar gamma ray is detected in the gamma ray detector 20; they typically are event data that include a coincident measurement check signal "0" and that thus include location information (x, y) but no energy information E. As mentioned in connection with the first example, annihilation or the like may cause a gamma ray other than a peculiar gamma ray to be incident on the gamma ray detector 20, in which case the coincident measurement check signal in the event data may indicate "1"; even then, if the energy information E in the same event data does not indicate energy $E_1$, those event data are classified as event data on an event that is not accompanied by detection of a peculiar gamma ray.

The location information (x, y) in each unit of event data in the group of event data 811 represents the X- and Y-axis components of the location of the type B nuclide $NC_{B1}$ in the imaging target TG. Thus, the image reconstructor 32 can generate a distribution image 821 of the type B nuclide $NC_{B1}$ in the imaging target TG by histograming the location information (x, y) in each unit of event data in the group of event data 311 on XY-plane.

That is, the imaging processor 30 can generate a distribution image 821 of the type B nuclide $NC_{B1}$ by using the location information (x, y) acquired when the time difference between the time point of beta ray detection by the beta ray detector 10 and the time point of gamma ray detection by the gamma ray detector 20 is equal to or less than the predetermined time $T_{TH}$ (that is, the coincident measurement check signal indicates "1") and in addition the energy information $E_1$ is obtained. In other words, the imaging processor 30 can generate a distribution image 821 of the type B nuclide $NC_{B1}$ by using the location information (x, y) in event data that indicate detection of a peculiar gamma ray with energy $E_1$ in the gamma ray detector 20 within the predetermined time $T_{TH}$ of the time point of beta ray detection by the beta ray detector 10.

In the eighth example, the type B nuclide $NC_{B1}$ is the only nuclide that emits a peculiar gamma ray; thus, each event is of one of the two types: one in which a peculiar gamma ray is detected or one in which no peculiar gamma ray is detected. Accordingly, the gamma ray detector 20 has only to check whether or not a peculiar gamma ray is detected. Then, the imaging processor 30 can generate a distribution image 821 of the type B nuclide $NC_{B1}$ by using the location information (x, y) of events in which the time difference between the time point of beta ray detection by the beta ray detector 10 and the time point of gamma ray detection by the gamma ray detector 20 is equal to or less than the predetermined time $T_{TH}$ (that is, the coincident measurement check signal indicates "1") and in addition a peculiar gamma ray is detected.

The location information (x, y) in each unit of event data in the group of event data 810 represents the detected values of the X- and Y-axis components of the presence location of the type B nuclide $NC_{B1}$ in the imaging target TG. Here, the location information (x, y) in each unit of event data in the group of event data 810 includes, in addition to location information based on detection of a beta ray by the beta ray detector 10, location information based on detection of a gamma ray (which can be a peculiar gamma ray) by the beta ray detector 10. Accordingly, histograming on XY-plane the location information (x, y) in every unit of event data in the group of event data 810 in the image reconstructor 32 results in generating an image 820 as if having the beta and gamma rays detected in the beta ray detector 10 superposed on each other. The image 820 is something like an image spread over a wider range than a distribution image 821 of the type B nuclide $NC_{B1}$ generated based on the event data 811, and is similar to the mage $IM_{\beta\gamma}$ shown in FIG. 19B.

On the other hand, the event data on which the distribution image 821 is based is data on events in which a beta ray and a peculiar gamma ray are detected coincidentally, and in those events, no gamma ray (which may be a peculiar gamma ray) is incident on the beta ray detector 10. Accordingly, the image generated from the location information of those events (that is, the distribution image 821) can be said to show only the distribution of beta rays in an extracted manner, and has high resolution. In this way, with the imaging apparatus 1, it is possible to image a single type B nuclide with high resolution.

With respect to the imaging apparatus 1 according to the embodiment, in the first to seventh examples described previously, it is assumed that preparing a beta ray detector 10 with a thickness necessary and sufficient (minimum required thickness, typically several millimeters or less) to reliably shield beta rays from nuclides used in imaging permits most gamma rays to penetrate the beta ray detector 10; accordingly, it is supposed that a beta ray detection signal from the beta ray detector 10 includes no location information based on detection of a gamma ray. The configuration described as the eighth example can be said to be useful in cases where gamma rays detected in the beta ray detector 10 constitute unignorable noise. Needless to say, detection of gamma rays in the beta ray detector 10 cannot be completely eliminated; thus, depending on cases, the imaging apparatus 1 according to the embodiment contributes, to one degree or another, to higher resolution in distribution images of type B nuclides than the reference imaging apparatus.

Considering that the beta ray detector 10 can detect not only beta rays but also gamma rays, the beta ray detector 10 can be defined also as follows.

The beta ray detector 10 receives and thereby detects radiation emitted from a radioactive nuclide in an imaging target TG; every time the beta ray detector 10 detects incidence of radiation on it, it outputs a beta ray detection signal. Although the radiation detected by the beta ray detector 10 is mainly beta rays, considering that the radiation detected by the beta ray detector 10 can be gamma rays, a beta ray detection signal from the beta ray detector 10 can be read as a radiation detection signal, and thus the radiation detection signal indicates incidence of radiation on the beta ray detector 10 and in addition includes location information indicating the detection location of the radiation in the beta ray detector 10. Likewise, considering that the radiation detected by the beta ray detector 10 can be gamma rays, the above-mentioned time point of beta ray detection can be read as the time point of radiation detection by the beta ray detector 10.

Ninth Example

A ninth example will be described. In the imaging processor 30, the process of forming a distribution image of a target nuclide from a beta ray detection signal and a gamma ray detection signal is implemented basically as a combination of hardware and software. Some of the functions performed by the imaging processor 30 (for example, the process of deriving location information from the output signal of the gamma ray detector 20, and the process for coincident measurement checking) can be implemented as hardware or software. In particular, in a case where coincident measurement checking is implemented as software, the data that constitutes event data, that is, the data of an output signal of the beta ray detector 10 and the data of an output signal of the gamma ray detector 20 are, with a common time stamp added to them, accumulated in a memory (unillustrated), and with respect to the accumulated data, coincident measurement checking is performed on a software basis based on the time stamp.

When a particular function is implemented as software, the particular function can be coded as a program so that running the program on a program execution device (for example, a microcomputer constituting the imaging processor 30) permits the function to be performed. Such a program can be stored and fixed in any recording medium. A recording medium in which the program is stored and fixed can be incorporated in, or connected to, a device (such as a server) separate from the imaging processor 30.

Tenth Example

A tenth example will be described. On the imaging apparatus 1, as a type A nuclide, any nuclide that undergoes type A radioactive decay can be used and, as a type B nuclide, any nuclide that undergoes type B radioactive decay can be used.

For example, as a type A nuclide that emits a positron by positive beta decay, any one or more of the nuclides $^{11}$C, $^{13}$N, and $^{18}$F can be taken as a type A nuclide to be contained in the imaging target TG. It should be noted that the just enumerated nuclides are typical ones that, after positive beta decay, transit to the ground state of the daughter nucleus with a probability of 100%, and that any other nuclide that, by positive beta decay, transits to the ground state of the daughter nucleus without going through the excited state of the daughter nucleus with a high probability can be regarded and used as a type A nuclide that undergoes positive beta decay.

For example, as a type A nuclide that undergoes negative beta decay (beta decay accompanied by emission of an electron), any one or more of the nuclides $^{32}$P, $^{33}$P, $^{42}$Ar, $^{66}$Ni, $^{90}$Y, $^{106}$Ru, $^{118}$Cd, $^{121}$Sn, $^{143}$Pr, $^{209}$Pb, and $^{210}$Pb can be taken as a type A nuclide to be contained in the imaging target TG. It should be noted that the just enumerated nuclides are typical ones that, after negative beta decay, transit to the ground state of the daughter nucleus with a probability of 100%, and that any other nuclide that, by negative beta decay, transits to the ground state of the daughter nucleus without going through the excited state of the daughter nucleus with a high probability can be regarded and used as a type A nuclide that undergoes negative beta decay.

For example, as a type B nuclide that emits a positron by positive beta decay, any one or more of the nuclides $^{14}$O, $^{22}$Na, $^{34m}$Cl, $^{38}$K, $^{44}$Sc, $^{48}$V, $^{52}$Mn, $^{52m}$Mn, $^{52}$Fe, $^{60}$Cu, $^{72}$As, $^{76}$Br, $^{82m}$Rb, $^{94m}$Tc, $^{104m}$Ag, $^{110m}$In, and $^{124}$I can be taken as a type B nuclide to be contained in the imaging target TG. It should be noted that the just enumerated nuclides are typical ones that emit a peculiar gamma ray with a probability of about 90%, and that any other nuclide with a lower emission probability than those can be used.

For example, as a type B nuclide that undergoes negative beta decay (beta decay accompanied by emission of an electron), any one or more of the nuclides $^{24}$Na, $^{27}$Mg, $^{38}$S, $^{43}$K, $^{46}$Sc, $^{47}$Ca, $^{48}$Sc, $^{55}$Mn, $^{60}$Co, $^{72}$Nn, $^{72}$Ga, $^{78}$Ge, $^{82}$Br, $^{92}$Sr, $^{95}$Nb, $^{96}$Nb, $^{103}$Ru, $^{130}$I, $^{132}$I, $^{134}$Cs, $^{135}$Xe, $^{148m}$Pm, $^{160}$Tb, $^{192}$Ir, $^{198}$Au, and $^{203}$Hg can be taken as a type B nuclide to be contained in the imaging target TG. It should be noted that the just enumerated nuclides are typical ones that emit a peculiar gamma ray with a probability of about 90%, and that any other nuclide with a lower emission probability than those can be used.

The method disclosed in Patent Document 1 (Japanese Patent registered as No. 5526435) exploits annihilation that results from emission of a positron, and thus can only use nuclides that undergo positive beta decay. By contrast, the imaging apparatus 1 according to the embodiment employs a method of directly imaging beta rays, and thus can use not only nuclides that undergo positive beta decay but also nuclides that undergo negative beta decay. This brings a great advantage.

For example, $^{24}$Na, which is a radioactive isotope of sodium, and $^{47}$Ca, which is a radioactive isotope of calcium, are type B nuclides that undergo negative beta decay, and thus cannot be used with the method of Patent Document 1, but can be used on the imaging apparatus 1 according to the embodiment. As is well known, sodium and calcium play an important role in life-sustaining actions. Thus, using $^{24}$Na and $^{47}$Ca as type B nuclides and imaging them in a discriminable manner on the imaging apparatus 1 makes it possible to know simultaneously the behavior of sodium and calcium in the living body as the imaging target TG. Or, imaging as the imaging target TG a living body that contains a plurality of radioactive nuclides including $^{47}$Ca makes it possible to know the behavior of calcium in the living body in a manner discriminable from that of other nuclides (the same applies to sodium).

Some radioactive nuclides dominantly do not emit a peculiar gamma ray in the process of transiting from the parent nucleus to the ground state of the daughter nucleus but still emit a peculiar gamma ray with a low probability (for example, with a probability less than 1%). Such radioactive nuclides should strictly be classified into type B nuclides, but can be handled also as type A nuclides on the imaging apparatus 1.

Radioactive nuclides that emit a peculiar gamma ray with a low probability but that are handled as type A nuclides on the imaging apparatus 1 will be referred to as quasi-type A nuclides. A peculiar gamma ray that can be emitted from a quasi-type A nuclide is disregarded in image reconstruction processing in the imaging processor 30. For example, in the third example, which corresponds to FIG. 14, in a case where a quasi-type A nuclide is used as the type A nuclide $NC_{N1}$, if the energy information E included in a gamma ray detection signal associated with a given event does not indicate energy $E_1$ or $E_2$, then, irrespective of a coincident measurement check signal, that event is handled as an event that is not accompanied by detection of a peculiar gamma ray, and the event data on the same event can be classified into the group of event data 410 (it is here assumed that the energy of the peculiar gamma ray that can be emitted from the quasi-type A nuclide differs from either of energies $E_1$ and $E_2$ and can be discriminated by the gamma ray detector that is used).

Some nuclides that undergo type B radioactive decay do transit to the excited state after beta decay but have a very long half-life as the life-span of the excited state (called nuclear isomers or, simply, isomers). The half-life of the excited state ranges from one nanosecond or less to years; if the life-span is equal to or longer than the time window of coincident measurement, the emission of a positron or electron and the emission of a peculiar gamma ray are not detected as occurring successively, and thus the peculiar gamma ray cannot be used for discrimination of a nuclide.

With a PET system, a nuclide that emits a positron by positive beta decay is used in imaging. However, positive beta decay does not always results in emission of a positron; positron emission competes with electron capture (the phenomenon in which a proton captures an electron orbiting around the atomic nucleus and turns into a neutron). That is, the two processes, positron emission and electron capture, compete with each other, with the result that only one of them takes place. The probabilities with which positron emission and electron capture respectively occur depend on the nuclide. However, because some nuclides undergo positive beta decay exclusively through electron capture and some other nuclides undergo positive beta decay dominantly through electron capture, not all positive beta decay nuclides can be used in PET imaging.

When positive beta decay through electron capture occurs, no positron is emitted, but a void is left in the orbit of the electron that is captured. Thus, when an electron transits to that orbit from an outer orbit, the extra energy is emitted as a characteristic X-ray from the positive beta decay nuclide. Using a detector sufficiently thick to absorb the characteristic X-ray permits the characteristic X-ray to be incident on the imaging apparatus 1, and thus imaging is then in principle possible as with a beta ray.

In the present invention, unlike a PET system, it is possible to use negative beta decay nuclides. However, as mentioned above, in positive beta decay, positron emission and electron capture compete with each other. Thus, the probability with which a positron is emitted depends on the nuclide, and some nuclides do not emit a positron. On the other hand, in negative beta decay, an electron is necessarily emitted. Thus, a larger number of negative beta decay nuclides are usable in the present invention.

Moreover, negative beta decay nuclides have neutrons in excess, and thus can be produced through irradiation with neutrons in a nuclear reactor or the like. They are thus generally less expensive than positive beta decay nuclides, which have positrons in excess and which require irradiation with charged particles in an accelerator such as a cyclotron.

Eleventh Example

An eleventh example will be described. As has been discussed above, a peculiar gamma ray has an energy peculiar to a nuclide; thus, by measuring it, it is possible to identify the nuclide. This, it should be noted, assumes that all the energy of the peculiar gamma ray is detected in the gamma ray detector 20. In reality, however, what takes place in the gamma ray detector 20 is not only total energy absorption but also partial energy absorption by Compton scattering or the like. In particular, in partial energy absorption by Compton scattering, the absorbed energy varies continuously with the scattering angle; thus, in the energy spectrum obtained from the results of detection by the gamma ray detector 20, a component corresponding to partial energy absorption appears, as a continuous component, in the part of the spectrum lower in energy than the peak resulting from total energy absorption. Thus, in a case where the imaging target TG contains a first type B nuclide that emits a first peculiar gamma ray having a relatively high energy and a second type B nuclide that emits a second peculiar gamma ray having a relatively low energy, the spectrum component resulting from partial energy absorption of the first peculiar gamma ray and the spectrum component resulting from total energy absorption of the second peculiar gamma ray overlap. It can also occur that those spectrum components overlap the spectrum component resulting from total or partial energy absorption of an annihilation gamma ray of a positron (a 511 keV gamma ray resulting from annihilation).

In the energy spectrum obtained from the results of detection by the gamma ray detector 20, a continuous component resulting from partial energy absorption that is observed on the lower or higher side of the peak corresponding to total energy absorption can be regarded as the same as a continuous component that overlaps the peak; then, by subtracting the continuous component from the peak part, it is possible to eliminate the background due to the overlap between them. Moreover, by using as the gamma ray detector 20 a gamma ray detector with a sufficiently high energy resolution and reducing the peak width ascribable to total energy absorption events (events accompanied by total energy absorption in the gamma ray detector 20), it is possible to reduce the background due to the overlap.

With partial energy absorption events (events accompanied by partial energy absorption in the gamma ray detector 20), it is possible to improve the efficiency of detection of peculiar gamma rays in the following manner. For the sake of concrete description, attention is paid to the above-discussed type B nuclide $NC_{B1}$, which emits a peculiar gamma ray with energy $E_1$. When a peculiar gamma ray from the type B nuclide $NC_{B1}$ undergoes partial energy absorption in the gamma ray detector 20, an energy less than energy $E_1$ is detected in the gamma ray detector 20. Here, a judgment can be made such that, if an energy equal to or more than a predetermined energy threshold value lower than energy $E_1$ is detected, it is judged that a peculiar gamma ray is detected. The energy threshold value can be set, with consideration given to the energy resolution of the gamma ray detector 20, within a range where a component ascribable to a gamma ray different from the peculiar gamma ray does not mix. Then, even if a peculiar gamma ray undergoes partial energy absorption, the peculiar gamma ray is detected; thus, improved detection efficiency for peculiar gamma rays is expected.

While, as described above, partial energy absorption events may lead to lower discrimination accuracy due to their overlapping with total energy absorption events of other nuclides, and setting an energy threshold value may help improve detection efficiency, the description of the examples presented above assumes, for the sake of concrete and simple description, a discrimination method that uses total energy absorption events.

As a technique for improved resolution, mention is made above of a known method of obtaining an enlarged image by use of a lens or the like that exploits refraction or reflection of scintillation light (visible light). Of different methods of the sort, any that can count scintillation light every event can be applied to the present invention.

Studies on the Present Invention

To follow are studies on the present invention.

An imaging apparatus $W_1$ according to one aspect of the present invention (see, for example, FIGS. 5 and 12 in particular) is a beta-emission two-dimensional imaging apparatus that includes:

a beta ray detector (10) configured to receive, from an imaging target (TG) containing a first nuclide (for example, a type B nuclide $NC_{B1}$) and a second nuclide (for example, a type B nuclide $NC_{B2}$), a beta ray based on the first or second nuclide and thereby detect the beta ray, the beta ray detector outputting a beta ray detection signal including location information indicating the detection location of the beta ray on a two-dimensional basis, the first nuclide transiting to an excited state of the daughter nucleus by beta decay and, subsequently to emission of a beta ray by beta decay, transiting to the ground state of the daughter nucleus while emitting a first peculiar gamma ray, the second nuclide transiting to an excited state of the daughter nucleus by beta decay and, subsequently to emission of a beta ray by beta decay, transiting to the ground state of the daughter nucleus while emitting a second peculiar gamma ray having a different energy from the energy of the first peculiar gamma ray;

a gamma ray detector (20) configured to detect a gamma ray, the gamma ray detector detecting the first and second peculiar gamma rays in a discriminable manner; and an imaging processor (30) configured to be capable of generating a distribution image (for example, a distribution image 221) of the first nuclide and a distribution image (for example, a distribution image 222) of the second nuclide in a discriminable manner based on the time point of beta ray detection by the beta ray detector and the time point of gamma ray detection by the gamma ray detector, the location information included in the beta ray detection signal, and which of the first and second peculiar gamma rays is detected in the gamma ray detector.

This makes it possible to image the distribution of a plurality of nuclides at once in a manner that permits discrimination between the nuclides. Moreover, owing to the employment of a method that directly images a beta ray, it is possible to use not only a nuclide that undergoes positive beta decay but also a nuclide that undergoes negative beta decay. This is useful.

Specifically, for example, in the imaging apparatus $W_1$, the imaging processor can be configured to generate the distribution image of the first nuclide by using the location information obtained when the first peculiar gamma ray is detected within a predetermined time of the time point of beta ray detection and generate the distribution image of the second nuclide by using the location information obtained when the second peculiar gamma ray is detected within the predetermined time of the time point of beta ray detection.

An imaging apparatus $W_2$ according to another aspect of the present invention (see, for example, FIGS. 5 and 13 in particular) is a beta-emission two-dimensional imaging apparatus that includes:

a beta ray detector (10) configured to receive, from an imaging target (TG) containing a first nuclide (for example, a type B nuclide $NC_{B1}$) and a second nuclide (for example, a type A nuclide $NC_{A1}$), a beta ray based on the first or second nuclide and thereby detect the beta ray, the beta ray detector outputting a beta ray detection signal including location information indicating the detection location of the beta ray on a two-dimensional basis, the first nuclide transiting to an excited state of the daughter nucleus by beta decay and, subsequently to emission of a beta ray by beta decay, transiting to the ground state of the daughter nucleus while emitting a peculiar gamma ray having a predetermined energy, the second nuclide transiting to a ground state of the daughter nucleus by emitting a beta ray by beta decay;

a gamma ray detector (20) configured to detect a gamma ray which may be the peculiar gamma ray; and an imaging processor (30) configured to be capable of generating a distribution image (for example, a distribution image 321) of the first nuclide and another distribution image (for example, a distribution image 320 or a type A distribution image) reflecting the distribution of the second nuclide in a discriminable manner based on the time point of beta ray detection by the beta ray detector and the time point of gamma ray detection by the gamma ray detector, the location information included in the beta ray detection signal, and whether the peculiar gamma ray is detected in the gamma ray detector.

This makes it possible to image the distribution of a plurality of nuclides at once in a manner that permits discrimination between the nuclides. Moreover, owing to the employment of a method that directly images a beta ray, it is possible to use not only a nuclide that undergoes positive beta decay but also a nuclide that undergoes negative beta decay. This is useful.

Specifically, for example, in the imaging apparatus $W_2$, the imaging processor can be configured to generate the distribution image of the first nuclide by using the location information obtained when the peculiar gamma ray is detected within a predetermined time of the time point of beta ray detection and generate a distribution image having the distribution of the first nuclide and the distribution of the second nuclide superposed on each other by using the location information obtained otherwise.

In either of the imaging apparatuses $W_1$ and $W_2$, a nuclide that undergoes negative beta decay can be used as one or both of the first and second nuclides.

An imaging apparatus $W_3$ according to yet another aspect of the present invention (see, for example, FIGS. 5 and 18 in particular) is a beta-emission two-dimensional imaging apparatus that includes:

a beta ray detector (10) configured to receive, from an imaging target (TG) containing a first nuclide (for example, a positive beta decay nuclide $NC_{P1}$) and a second nuclide (for example, a negative beta decay nuclide $NC_{N1}$), a beta ray based on the first or second nuclide and thereby detect the beta ray, the beta ray detector outputting a beta ray detection signal including location information indicating the detection location of the beta ray on a two-dimensional basis, the first nuclide emitting a positron as a beta ray by positive beta decay, the second nuclide emitting an electron as a beta ray by negative beta decay;

a gamma ray detector (20) configured to detect a gamma ray which may be an annihilation gamma ray resulting from annihilation of the positron as the beta ray from the first nuclide with an electron in the beta ray detector; and an imaging processor (30) configured to be capable of generating a distribution image (for example, a distribution image 721) of the first nuclide and another distribution image (for example, a distribution image 720 or a negative beta decay nuclide distribution image) reflecting the distribution of the second nuclide in a discriminable manner based on the time point of beta ray detection by the beta ray detector and the time point of gamma ray detection by the gamma ray detector, the location information included in the beta ray detection signal, and whether the annihilation gamma ray is detected in the gamma ray detector.

This makes it possible to image the distribution of a plurality of nuclides at once in a manner that permits discrimination between the nuclides. Moreover, owing to the employment of a method that directly images a beta ray, it is possible to use not only a nuclide that undergoes positive beta decay but also a nuclide that undergoes negative beta decay. This is useful.

Specifically, for example, in the imaging apparatus $W_3$, the imaging processor can be configured to generate the distribution image of the first nuclide by using the location information obtained when the annihilation gamma ray is detected within a predetermined time of the time point of beta ray detection and generate a distribution image having a distribution of the first nuclide and the distribution of the second nuclide superposed on each other by using the location information obtained otherwise.

An imaging method $W_{1A}$ according to a further aspect of the present invention is a beta-emission two-dimensional imaging method that includes:

a beta ray detecting step of receiving, from an imaging target containing a first nuclide and a second nuclide, a beta ray based on the first or second nuclide, thereby detecting the beta ray, and then obtaining a beta ray detection signal including location information indicating the detection location of the beta ray on a two-dimensional basis, the first nuclide transiting to an excited state of the daughter nucleus by beta decay and, subsequently to emission of a beta ray by beta decay, transiting to the ground state of the daughter nucleus while emitting a first peculiar gamma ray, the second nuclide transiting to an excited state of the daughter nucleus by beta decay and, subsequently to emission of a beta ray by beta decay, transiting to the ground state of the daughter nucleus while emitting a second peculiar gamma ray having a different energy from the energy of the first peculiar gamma ray;

a gamma ray detecting step of detecting a gamma ray, the gamma ray detecting step involving detecting the first and second peculiar gamma rays in a discriminable manner; and an imaging processing step capable of generating a distribution image of the first nuclide and a distribution image of the second nuclide in a discriminable manner based on the time point of beta ray detection in the beta ray detecting step and the time point of gamma ray detection in the gamma ray detecting step, the location information included in the beta ray detection signal, and which of the first and second peculiar gamma rays is detected in the gamma ray detecting step.

An imaging method $W_{2A}$ according to a further aspect of the present invention is a beta-emission two-dimensional imaging method that includes:

a beta ray detecting step of receiving, from an imaging target containing a first nuclide and a second nuclide, a beta ray based on the first or second nuclide, thereby detecting the beta ray, and then obtaining a beta ray detection signal including location information indicating the detection location of the beta ray on a two-dimensional basis, the first nuclide transiting to an excited state of the daughter nucleus by beta decay and, subsequently to emission of a beta ray by beta decay, transiting to the ground state of the daughter nucleus while emitting a peculiar gamma ray having a predetermined energy, the second nuclide transiting to the ground state of the daughter nucleus by emitting a beta ray by beta decay;

a gamma ray detecting step of detecting a gamma ray which may be the peculiar gamma ray; and an imaging processing step capable of generating a distribution image of the first nuclide and another distribution image reflecting the distribution of the second nuclide in a discriminable manner based on the time point of beta ray detection in the beta ray detecting step and the time point of gamma ray detection in the gamma ray detecting step, the location information included in the beta ray detection signal, and whether the peculiar gamma ray is detected in the gamma ray detecting step.

An imaging method $W_{3A}$ according to a further aspect of the present invention is a beta-emission two-dimensional imaging method that includes:

a beta ray detecting step of receiving, from an imaging target containing a first nuclide and a second nuclide, a beta ray based on the first or second nuclide, thereby detecting the beta ray, and then obtaining a beta ray detection signal including location information indicating the detection location of the beta ray on a two-dimensional basis, the first nuclide emitting a positron as a beta ray by positive beta decay, the second nuclide emitting an electron as a beta ray by negative beta decay;

a gamma ray detecting step of detecting a gamma ray which may be an annihilation gamma ray resulting from annihilation of the positron as the beta ray from the first nuclide with an electron in the beta ray detector; and an imaging processing step capable of generating a distribution image of the first nuclide and another distribution image reflecting the distribution of the second nuclide in a discriminable manner based on the time point of beta ray detection in the beta ray detecting step and the time point of gamma ray detection in the gamma ray detecting step, the location information included in the beta ray detection signal, and whether the annihilation gamma ray is detected in the gamma ray detecting step.

An imaging apparatus $W_4$ according to still another aspect of the present invention (see, for example, FIGS. 5 and 20 in particular) is a beta-emission two-dimensional imaging apparatus that includes:

a beta ray detector (10) configured to receive, from an imaging target (TG) containing a nuclide (for example, a type B nuclide $NC_{B1}$), a beta ray based on the nuclide and thereby detect the beta ray, the beta ray detector outputting a beta ray detection signal including location information indicating the detection location of the beta ray on a two-dimensional basis, the nuclide transiting to an excited state of the daughter nucleus by beta decay and, subsequently to emission of a beta ray by beta decay, transiting to the ground state of the daughter nucleus while emitting a peculiar gamma ray, a gamma ray detector (20) configured to detect a gamma ray which may be the peculiar gamma ray; and an imaging processor (30) configured to be capable of generating a distribution image (for example, a distribution image 821) of the nuclide based on the time point of beta ray detection by the beta ray detector and the time point of gamma ray detection by the gamma ray detector, the location information included in the beta ray detection signal, and whether the peculiar gamma ray is detected in the gamma ray detector.

While the beta ray detector is intended to detect a beta ray from the nuclide present in the imaging target, a gamma ray from the nuclide may be detected in the beta ray detector. Here, the beta ray detector cannot detect the beta and gamma rays in a discriminable manner, and thus the location information in the beta ray detection signal includes, in addition to location information indicating the detection location of the beta ray, location information indicating the detection location of the gamma ray in a form undiscriminable from each other. The location information indicating the detection location of the gamma ray acts as noise and, if no gamma ray detector is provided, degrades the resolution of the generated distribution image of the nuclide. This is because, since the gamma ray has a longer flying range than the beta ray, an image showing a distribution over a wider range than the actual distribution of the nuclide is generated (see FIG. 19B).

By contrast, with the imaging apparatus $W_4$ configured as described above, it is possible to generate a distribution image of the nuclide based on the location information obtained when the peculiar gamma ray is detected in the gamma ray detector. When the peculiar gamma ray is detected in the gamma ray detector, the peculiar gamma ray is not incident on the beta ray detector. Thus, the location information obtained when the peculiar gamma ray is detected in the gamma ray detector is limited to information on the detection location of a beta ray. By generating a distribution image of the nuclide based on that detection location information, it is possible to generate a distribution image with high resolution, with the above-mentioned noise excluded.

Specifically, for example, in the imaging apparatus $W_4$, the imaging processor can be configured to generate the distribution image of the nuclide by using the location information obtained when the peculiar gamma ray is detected within a predetermined time of the time point of beta ray detection.

An imaging method $W_{44}$ according to a further aspect of the present invention is a beta-emission two-dimensional imaging method that includes:

a beta ray detecting step of receiving, from an imaging target containing a nuclide, a beta ray based on the nuclide, thereby detecting the beta ray, and then obtaining a beta ray detection signal including location information indicating the detection location of the beta ray on a two-dimensional basis, the nuclide transiting to an excited state of the daughter nucleus by beta decay and, subsequently to emission of a beta ray by beta decay, transiting to the ground state of the daughter nucleus while emitting a peculiar gamma ray, a gamma ray detecting step of detecting a gamma ray which may be the peculiar gamma ray; and an imaging processing step capable of generating a distribution image of the nuclide based on the time point of beta ray detection in the beta ray detecting step and the time point of gamma ray detection in the gamma ray detecting step, the location information included in the beta ray detection signal, and whether the peculiar gamma ray is detected in the gamma ray detecting step.

The embodiments of the present invention allow for many modifications made as necessary within the scope of the technical concept set forth in the appended claims. The embodiments described above are merely examples of how the present invention can be implemented, and the senses of the terms used to define the present invention and its features are not limited to those in which they are used in the description of the embodiments given above. All specific values mentioned in the above description are merely examples, and can naturally be altered to different values.

LIST OF REFERENCE SIGNS 1 imaging apparatus
10 beta ray detector
20 gamma ray detector
30 imaging processor
31 coincident measurement checker
32 image reconstructor
TG imaging target

The invention claimed is:

1. An apparatus for beta-emission two-dimensional imaging, comprising:

a beta ray detector configured to receive, from an imaging target containing a first nuclide and a second nuclide, a beta ray based on the first or second nuclide and thereby detect the beta ray, the beta ray detector outputting a beta ray detection signal including location information indicating a detection location of the beta ray on a two-dimensional basis, the first nuclide transiting to an excited state of a daughter nucleus by beta decay and, subsequently to emission of a beta ray by beta decay, transiting to a ground state of the daughter nucleus while emitting a peculiar gamma ray having a predetermined energy, the second nuclide transiting to a ground state of a daughter nucleus by emitting a beta ray by beta decay;

a gamma ray detector disposed separately from the beta ray detector and configured differently from the beta ray detector to detect a gamma ray which may be the peculiar gamma ray; and an imaging processor configured to be capable of generating a distribution image of the first nuclide and another distribution image reflecting a distribution of the second nuclide in a discriminable manner based on a time point of beta ray detection by the beta ray detector and a time point of gamma ray detection by the gamma ray detector, the location information included in the beta ray detection signal, and whether the peculiar gamma ray is detected in the gamma ray detector, wherein the imaging processor is configured to generate the distribution image of the first nuclide by using the location information obtained when the peculiar gamma ray is detected within a predetermined time of the time point of beta ray detection, generate a distribution image having a distribution of the first nuclide and the distribution of the second nuclide superposed on each other by using the location information obtained otherwise, and generate a distribution image of the second nuclide by synthesizing together:

the distribution image of the first nuclide, and
the distribution image having the distribution of the first nuclide and the distribution of the second nuclide superposed on each other.

2. An apparatus for beta-emission two-dimensional imaging, comprising:
a beta ray detector configured to receive, from an imaging target containing a first nuclide and a second nuclide, a beta ray based on the first or second nuclide and thereby detect the beta ray, the beta ray detector outputting a beta ray detection signal including location information indicating a detection location of the beta ray on a two-dimensional basis, the first nuclide emitting a positron as a beta ray by positive beta decay, the second nuclide emitting an electron as a beta ray by negative beta decay;
a gamma ray detector disposed separately from the beta ray detector and configured differently from the beta ray detector to detect a gamma ray which may be an annihilation gamma ray resulting from annihilation of the positron as the beta ray from the first nuclide with an electron in the beta ray detector; and
an imaging processor configured to be capable of generating a distribution image of the first nuclide and another distribution image reflecting a distribution of the second nuclide in a discriminable manner based on
a time point of beta ray detection by the beta ray detector and a time point of gamma ray detection by the gamma ray detector,
the location information included in the beta ray detection signal, and
whether the annihilation gamma ray is detected in the gamma ray detector, wherein the imaging processor is configured to
generate the distribution image of the first nuclide by using the location information obtained when the annihilation gamma ray is detected within a predetermined time of the time point of beta ray detection,
generate a distribution image having a distribution of the first nuclide and the distribution of the second nuclide superposed on each other by using the location information obtained otherwise, and
generate a distribution image of the second nuclide by synthesizing together:
the distribution image of the first nuclide, and
the distribution image having the distribution of the first nuclide and the distribution of the second nuclide superposed on each other.

3. A method for beta-emission two-dimensional imaging, comprising:
a beta ray detecting step of receiving, from an imaging target containing a first nuclide and a second nuclide, a beta ray based on the first or second nuclide, thereby detecting the beta ray, and then obtaining a beta ray detection signal including location information indicating a detection location of the beta ray on a two-dimensional basis,
the first nuclide transiting to an excited state of a daughter nucleus by beta decay and, subsequently to emission of a beta ray by beta decay, transiting to a ground state of the daughter nucleus while emitting a peculiar gamma ray having a predetermined energy,
the second nuclide transiting to a ground state of a daughter nucleus by emitting a beta ray by beta decay;

a gamma ray detecting step of detecting a gamma ray which may be the peculiar gamma ray; and
an imaging processing step capable of generating a distribution image of the first nuclide and another distribution image reflecting a distribution of the second nuclide in a discriminable manner based on
a time point of beta ray detection in the beta ray detecting step and a time point of gamma ray detection in the gamma ray detecting step,
the location information included in the beta ray detection signal, and
whether the peculiar gamma ray is detected in the gamma ray detecting step, wherein the beta ray detecting step is performed by using a beta ray detector,
the gamma ray detecting step is performed by using a gamma ray detector disposed separately from the beta ray detector and configured differently from the beta ray detector, and
in the imaging processing step,
the distribution image of the first nuclide is generated by using the location information obtained when the peculiar gamma ray is detected within a predetermined time of the time point of beta ray detection,
a distribution image having a distribution of the first nuclide and the distribution of the second nuclide superposed on each other is generated by using the location information obtained otherwise, and
a distribution image of the second nuclide is generated by synthesizing together:
the distribution image of the first nuclide, and
the distribution image having the distribution of the first nuclide and the distribution of the second nuclide superposed on each other.

4. A method for beta-emission two-dimensional imaging, comprising:
a beta ray detecting step of receiving, from an imaging target containing a first nuclide and a second nuclide, a beta ray based on the first or second nuclide, thereby detecting the beta ray, and then obtaining a beta ray detection signal including location information indicating a detection location of the beta ray on a two-dimensional basis, the first nuclide emitting a positron as a beta ray by positive beta decay, the second nuclide emitting an electron as a beta ray by negative beta decay;
a gamma ray detecting step of detecting a gamma ray which may be an annihilation gamma ray resulting from annihilation of the positron as the beta ray from the first nuclide with an electron in a beta ray detector used in the beta ray detecting step; and
an imaging processing step capable of generating a distribution image of the first nuclide and another distribution image reflecting a distribution of the second nuclide in a discriminable manner based on
a time point of beta ray detection in the beta ray detecting step and a time point of gamma ray detection in the gamma ray detecting step,
the location information included in the beta ray detection signal, and
whether the annihilation gamma ray is detected in the gamma ray detecting step, wherein
the gamma ray detecting step is performed by using a gamma ray detector disposed separately from the beta ray detector and configured differently from the beta ray detector, and in the imaging processing step, the distribution image of the first nuclide is generated by using the location information obtained when the annihilation gamma ray is detected within a predetermined time of the time point of beta ray detection, a distribution image having a distribution of the first nuclide and the distribution of the second nuclide superposed on each other is generated by using the location information obtained otherwise, and a distribution image of the second nuclide is generated by synthesizing together:
the distribution image of the first nuclide, and
the distribution image having the distribution of the first nuclide and the distribution of the second nuclide superposed on each other.

5. The apparatus according to claim 1, wherein a nuclide that undergoes negative beta decay can be used as one or both of the first and second nuclides.

* * * * *